(12) United States Patent
Li et al.

(10) Patent No.: US 8,940,719 B2
(45) Date of Patent: Jan. 27, 2015

(54) LITHOCHOLIC ACID ANALOGUES THAT INHIBIT SIALYLTRANSFERASE

(75) Inventors: Wen-Shan Li, Taipei (TW); Yi-Ching Wang, Taipei (TW); Hsueh-Fen Juan, Taipei (TW)

(73) Assignee: Academia Sinica, Taipei (TW)

( * ) Notice: Subject to any disclaimer, the term of this patent is extended or adjusted under 35 U.S.C. 154(b) by 929 days.

(21) Appl. No.: 11/481,131

(22) Filed: Jul. 3, 2006

(65) Prior Publication Data

US 2008/0119443 A1 May 22, 2008

(51) Int. Cl.
*A61K 31/58* (2006.01)
*C07J 43/00* (2006.01)
*C07J 1/00* (2006.01)
*C07J 51/00* (2006.01)

(52) U.S. Cl.
CPC ... *C07J 1/00* (2013.01); *C07J 51/00* (2013.01)
USPC .......................................... 514/176; 540/108

(58) Field of Classification Search
CPC .............................. C07J 43/003; A61K 31/58
USPC ........... 514/176, 177, 182; 540/108; 552/176, 552/177, 182, 548, 552
See application file for complete search history.

(56) References Cited

U.S. PATENT DOCUMENTS

| 6,846,812 B2 * | 1/2005 | Dalko et al. ................ 514/171 |
| 2002/0115623 A1 | 8/2002 | Wu et al. |

FOREIGN PATENT DOCUMENTS

| JP | 61083125 A | 4/1986 |
| JP | 8198891 A | 8/1996 |
| JP | 8198892 A | 8/1996 |
| JP | 10330364 A | 12/1998 |
| WO | WO 98/00169 * | 1/1998 |
| WO | WO 00/08040 A1 | 2/2000 |
| WO | WO 2004/006939 A1 | 1/2004 |

OTHER PUBLICATIONS

Vippagunta et al. (Advanced Drug Delivery Reviews, 48 (2001), pp. 3-26).*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Chang et al., "Lithocholic acid analogues, new and potent alpha-2,3-sialyltransferase inhibitors". Chem. Commun., Jan. 2006, pp. 629-631.*
Jurutka et al., "Molecular and functional comparison of 1,25-dihydroxyvitamin D3 and the novel vitamin D receptor ligan, lithocholic acid, in activating transcription of cytochrome P450 3A4". Journal of cellular biochemistry, vol. 94, 2005, pp. 917-943.*
Kuramoto et al., "Intestinal absorption and metabolism of homoursodeoxycholic acid in rats." J. of Pharmacobio-Dynamics, vol. 10(7), pp. 309-316, 1987 (Abstract only).*
Barton et al., "Functionalization of saturated hydrocarbons. Part 13. Further studies on the Gif oxidation of cholestane derivatives.", Journal of the Chemical Society, Perkin Transactions 1, (3), pp. 463-468, 1989.*
Herz et al., "Synthesis of steroidal nitroimidazoles." Organic Preparations and Procedures International, 7(4), pp. 211-213, 1975.*
Ono et al., "Synthese and preventive effects of analogs related to 1alpha,25-dihydroxy-2beta-(3-hydroxypropoxy) vitamin D3 (ED-71) on bone mineral loss in ovariectomized rats." Bioorganic & Medicinal Chemistry, 6(12), 2517-2523, 1998.*
Shaikh et al., "Synthesis and mesomorphic behaviour of lithocholic acid derivatives." Bull. Mater. Sci., vol. 26(5), pp. 559-563.*
Mizushina et al., "Structural relationship of lithocholic acid derivatives binding to the N-terminal 8-kDa domain of DNA polymerase beta." Biochemistry, vol. 43, pp. 10669-10677.*
Chang et al., "Lithocholic Acid Analogues, New and Potent α-2,3-sialyltransferase Inhibitors," Chem. Commun., 629-631 (2006).
Drinnan et al., "Inhibitors of Sialyltransferases: Potential Roles in Tumor Growth and Metastasis," Mini Reviews in Medicinal Chemistry, 3: 501-517 (2003).
Ellington et al., "Inhibition of Akt Signaling and Enhanced ERK1/2 Activity are Involved in Induction of Macroautophagy by Triterpenoid B-group Soyasaponins in Colon Cancer Cells," Carcinogenesis, 27(2): 298-306 (2006).
Hsu et al., "Soyasaponin-I-modified Invasive Behavior of Cancer by Changing Cell Surface Sialic Acids," Gynecologic Oncology, 96:415-422 (2005).
Kang et al., "Soybean Saponins Suppress the Release of Proinflammatory Mediators by LPS-stimulated Peritoneal Macrophages," Cancer Letters, 230: 219-227 (2005).
Wu et al., "Soyasaponin I, a Potent and Specific Sialyltransferase Inhibitor," Biochemical and Biophysical Research Communications, 284: 466-469 (2001).

* cited by examiner

*Primary Examiner* — Barbara P Badio
(74) *Attorney, Agent, or Firm* — Hsiu-Ming Saunders; Intellectual Property Connections, Inc.

(57) ABSTRACT

Certain chemical entities chosen from compounds of Formula I:

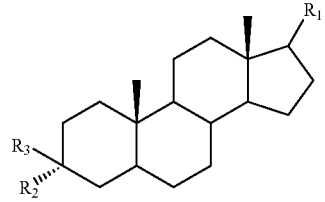

Formula I and pharmaceutically acceptable salts, solvates, chelates, non-covalent complexes, prodrugs, and mixtures thereof are described. Pharmaceutical compositions comprising at least one chemical entity chosen from compounds of Formula I and a pharmaceutically acceptable vehicle are described. Also described are methods for inhibiting α-2,3-sialyltransferase activity in cells, and methods for treating a patient having a disease responsive to inhibition of α-2,3-sialyltransferase activity.

24 Claims, 6 Drawing Sheets

LITHOCHOLIC ACID ANALOGUES THAT INHIBIT SIALYLTRANSFERASE

FIELD

Provided are certain membrane-permeable lithocholic acid analogues that inhibit α-2,3-sialyltransferase and pharmaceutical compositions comprising at least one membrane-permeable lithocholic acid analog that inhibits α-2,3-sialyltransferase activity. Also provided are methods of inhibiting α-2,3-sialyltransferase activity in a cell, and methods of treating a disease associated with α-2,3-sialyltransferase activity.

BACKGROUND

The glycosylation of cellular proteins and lipids is an integral part of many normal cellular functions, yet glycosylation, including sialylation, may also contribute to tumor cell formation, metastasis, and invasion. Sialylation is catalyzed by a family of sialyltransferases (STs) that transfer sialic acid, a nine-carbon amino sugar that is negatively charged under physiological conditions, to the terminal position of growing oligosaccharide chains of glycoconjugates. Hypersialylation plays a vital role in cellular adhesion, immune defense, and inflammation, yet altered ST activity is also implicated in tumor formation and invasion in many tumor models (Harvey et al., 1992; Majuri et al., 1995; Dall'Olio and Chiricolo, 2001; Wang et al., 2002). And specifically, the α sub-type ST, α-2,3-sialyltransferase (α-2,3-ST), is up-regulated by overexpression of the ras oncogene (Easton et al., 1991). The identification of potent ST inhibitors, therefore, represents a promising approach to the development of cancer therapies, including therapies directed at preventing metastasis.

A number of ST inhibitors have been developed. These include inhibitors with a structural mimetic of transition-state analogues, bisubstrate analogues, donor analogues, and acceptor analogues based on cytidine monophosphate-N-acetylneuraminic acid (CMP-Neu5Ac) or disaccharides (Skropeta et al., *Glycoconjugate J.,* 2004, 21:205; Chang, Tao and W.-S. Li, *Synlett,* 2004, 37; Whalen, McEvoy and Halcomb, *Bioorg. Med. Chem. Lett.,* 2003, 13:301; Schwoerer and Schmidt, *J. Am. Chem. Soc.,* 2002, 124:1632; Muller, Schaub and Schmidt, *Angew. Chem., Int. Ed.,* 1998, 37:2893). Although these compounds effectively inhibit STs, they display poor permeability across cell membranes and thus their clinical applications are limited. Similarly, ST inhibitors purified from natural products are available in only small quantities, limiting their availability for clinical use (Hsu et al., 2005).

It is accordingly an object of the present invention to provide novel lithocholic acid analogues and pharmaceutical compositions comprising these lithocholic acid analogues that potently inhibit α-2,3-ST and display improved membrane permeability for cellular uptake. It is a further object of the present invention to provide α-2,3-ST inhibitors that treat a disease responsive to inhibition of α-2,3-ST activity.

SUMMARY

Provided is at least one chemical entity chosen from compounds of Formula I:

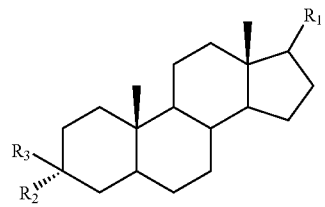

Formula I and pharmaceutically acceptable salts, solvates, chelates, non-covalent complexes, prodrugs, and mixtures thereof, wherein $R_1$ is optionally substituted alkyl; $R_2$ is chosen from hydroxy and acyloxy; $R_3$ is hydrogen, or $R_2$ and $R_3$, taken together with the carbon to which they are attached, form an oxo group; and provided that when $R_1$ is (R)-4-carboxybutan-2-yl, then $R_2$ is not hydroxy. Further provided is a pharmaceutical composition comprising a therapeutically effective amount of at least one chemical entity chosen from compounds of Formula I and a pharmaceutically acceptable vehicle.

Provided is a method for inhibiting α-2,3-sialyltransferase activity comprising contacting cells expressing α-2,3-sialyltransferase with at least one chemical entity chosen from compounds of Formula I in an amount sufficient to detectably decrease the level of sialylation of glycoconjugates. Further provided is a method for treating a patient having a disease responsive to inhibition of α-2,3-sialyltransferase activity comprising administering to the patient a therapeutically effective amount of at least one chemical entity chosen from compounds of Formula I.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory only and are not restrictive of the invention, as claimed. The accompanying drawings, which are incorporated in and constitute a part of this specification, illustrate several embodiments of the invention and together with the description, serve to explain the principles of the invention. In the specification and the appended claims, the singular forms "a," "an," and "the" include plural reference unless the context clearly dictates otherwise.

DESCRIPTION OF EMBODIMENTS

Figure 1:
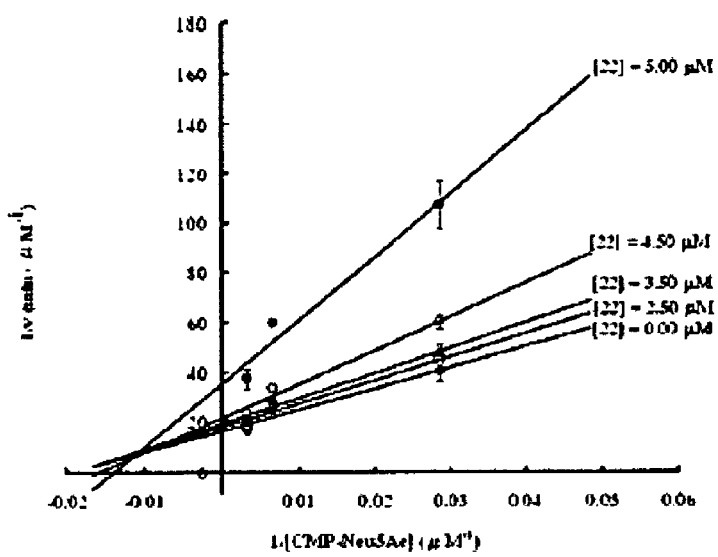
FIG. 1 shows a Lineweaver-Burk plot of the results of rat α-2,3-ST inhibition assay for the synthetic inhibitor 22.

Chemical entities of the present invention include, but are not limited to, compounds of Formula I, such as compounds of Table 1, and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Acyl" refers to a radical —C(O)R, where R is alkyl, substituted alkyl, substituted cycloalkyl, substituted heterocycloalkyl, substituted aryl, or substituted heteroaryl group as defined herein. Representative examples include, but are not limited to, acetyl, cylcohexylcarbonyl, cyclohexylmethylcarbonyl, benzoyl, benzylcarbonyl, and the like.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl; butanyls such as butan-1-yl, butan-2-yl (sec-butyl), 2-methyl-propan-1-yl (isobutyl), 2-methyl-propan-2-yl (t-butyl), cyclobutan-1-yl; and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkoxy" refers to a radical —OR where R represents an alkyl, substituted alkyl, substituted cycloalkyl, substituted heterocycloalkyl, substituted aryl, or substituted heteroaryl group as defined herein. Representative examples include, but are not limited to, methoxy, ethoxy, propoxy, butoxy, cyclohexyloxy, and the like.

"Alkoxycarbonyl" refers to a radical —C(O)— alkoxy where alkoxy is as defined herein.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms. In other embodiments, an alkyl group comprises from 1 to 6 carbon atoms, and is referred to as a lower alkyl group.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms.

"Amino" refers to the radical —NH$_2$.

"Aminocarbonyl" refers to the group —C(O)NRR' where R and R' are independently chosen from hydrogen, alkyl, substituted alkyl, substituted cycloalkyl, substituted heterocycloalkyl, substituted aryl, or substituted heteroaryl group as defined herein, or optionally R' and R" together with the nitrogen atom to which R and R' are attached form one or more heterocyclic or substituted heterocyclic rings.

"Aryl" encompasses: 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically a terminal or $Sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, and/or arylalkynyl is used. In certain embodiments, an arylalkyl group can be ($C_6$-30) arylalkyl, e.g., the alkanyl, alkenyl or alkynyl moiety of the arylalkyl group can be ($C_{1-10}$) and the aryl moiety can be ($C_{6-20}$).

"Aryloxycarbonyl" refers to a radical —C(O)—O—R wherein R is chosen from aryl and substituted aryl as defined herein.

"Carbonyl" refers to the radical —C(O).

As used herein, the terms "cancer" refers to or describes the physiological condition in an animal in which a population of cells are characterized by unregulated cell growth. Chemical compounds of the present disclosure are useful for the treatment of cancer, including, but not limited to, glioblastoma, ovarian cancer, breast cancer, endometrial carcinoma, hepatocellular carcinoma, melanoma, colorectal cancer, colon cancer, digestive tract, lung cancer, renal-cell carcinoma, thyroid, lymphoid, prostate cancer, pancreatic cancer, advanced tumors, hairy cell leukemia, melanoma, chronic myelygenous leukemia, advanced head and neck, squamous cell cancer, metastatic renal cell, non-Hodgkin's lymphoma, metastatic breast, breast adenocarcinoma, advanced melanoma, gastric, non-small cell lung, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer.

More particularly, cancers that may be treated by chemical compounds of the present disclosure, include, but are not limited to: Cardiac: sarcoma (angiosarcoma, fibrosarcoma, rhabdomyosarcoma, liposarcoma), myxoma, rhabdomyoma, fibroma, lipoma, teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous, cell carcinoma, adenocarcinoma, leiomyosarcoma, lymphoma) stomach (carcinoma, lymphoma, leiomyosarcoma), pancreas (ductal adenocarcinoma, insulinoma, glucagonoma, gastrinoma, carcinoid tumors, Karposi's sarcoma, leiomyoma, hemangioma, lipoma, neurofibroma, fibroma), large bowel (adenocarcinomas, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embroyonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chrodroma, chondroblastoma, chondromyxofibroma, osteoid osteoma and giant cell tumors; Nervous system: skull (osteoma, hemangioma, granuloma, xanthoma, osteitis deformans, meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenitial tumors), spinal cord, neurofibroma, meningioma, glioma, sarcoma); Gynecological: uterus (endometrial carcinoma), cervix (cervical carcinoma, pre-tumor cervical dsplasia), ovaries (ovarian carcinoma [serous cystadenocarcinoma, mucinous cystadenocarcinoma], granulose-thecal cell tumors, Sertoli-Leydig cell tumors, dysgerminoma, malignant teratoma), vulva (squamous cell carcinoma, intraepithelial carcinoma, adenocarcinoma, firosarcoma, melanoma) vagina (clear cell carcinoma, squamous cell carcinoma, botryoid sarcoma (embryonal rhabdomyosarcoma), fallopian tubes carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basel cell carcinoma, squamous cell carcinoma, Karposi's sarcoma, moles dysplastic nevi, lipoma, angioma, dermatofibroma, keloids, psoriasis; and Adrenal glands: neuroblastoma.

"Carboxy" refers to the radical —C(O)OH.

"Cleave" refers to breakage of chemical bonds and is not limited to chemical or enzymatic reactions or mechanisms unless clearly indicated by the context.

The term "chelate" refers to the chemical entity formed by the coordination of a compound to a metal ion at two (or more) points.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged saturated ring groups such as norbornane.

"Dialkylphosphonate" refers to the radical —PO(OR$_a$)(OR$_b$) where R$_a$ and R$_b$ are the same or different alkyl groups.

"Disease" refers to any disease, disorder, condition, symptom, and indication.

"Halogen" or "halo" refers to a fluoro, chloro, bromo, or iodo group.

"Heteroaryl" encompasses: 5- to 7-membered aromatic, monocyclic rings containing one or more (for example from 1 to 4, or in certain embodiments from 1 to 3) heteroatoms chosen from N, O, and S, with the remaining ring atoms being carbon; and bicyclic heterocycloalkyl rings containing one or more (for example from 1 to 4, or in certain embodiments from 1 to 3) heteroatoms chosen from N, O, and S, with the remaining ring atoms being carbon and wherein at least one heteroatom is present in an aromatic ring. For example, heteroaryl includes a 5- to 7-membered heterocycloalkyl aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above. In certain embodiments, heteroaryl groups can be those derived from thiophene, pyrrole, benzothiophene, benzofuran, indole, pyridine, quinoline, imidazole, oxazole, pyrazine, benzothiazole, isoxazole, thiadiaxole, and thiazole.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. In certain embodiments, the heteroarylalkyl group can be a 6 to 30 membered heteroarylalkyl, e.g., the alkanyl, alkenyl or alkynyl moiety of the heteroarylalkyl can be 1 to 10 membered and the heteroaryl moiety can be a 5 to 20-membered heteroaryl.

"Heterocycloalkyl" refers to a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (═O) or oxide (—O⁻) substituents, such as piperidinyl N-oxide, morpholinyl-N-oxide, 1-oxo-1-thiomorpholinyl and 1,1-dioxo-1-thiomorpholinyl.

The term "metastasis" and grammatical equivalents refers to the process by which a cancer spreads or transfers from the site of origin to other regions of the body with the development of a similar cancerous lesion at the new location. The process encompasses cancer cell migration from the site of origin and invasion of tissue at the new location.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

"Optional" or "optionally" means that the subsequently described event or circumstance may but need not occur, and that the description includes instances where the event or circumstance occurs and instances in which the event does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible, and inherently unstable.

"Patient" or "subject" refers to an animal, such as a mammal, that has been or will be the object of treatment, observation, or experiment. The methods of the invention can be useful in both human therapy and veterinary applications. In some embodiments, the patient is a mammal; and in some embodiments the patient is human.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound. Such salts include: (1) acid addition salts formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient, carrier or adjuvant" refers to an excipient, carrier or adjuvant that can be administered to a subject, together with at least one chemical entity of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one chemical entity of the present disclosure is administered.

"Prodrug" refers to a derivative of a therapeutically effective compound that requires a transformation within the body to produce the therapeutically effective compound. Prodrugs can be pharmacologically inactive until converted to the parent compound.

"Protecting group" refers to a grouping of atoms that when attached to a reactive group in a molecule masks, reduces, or prevents that reactivity. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitro-veratryloxycarbonyl ("NVOC"), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

The term "therapeutically effective amount" of a chemical entity of this invention means an amount effective, when administered to a human or non-human patient, to provide a therapeutic benefit such as amelioration of symptoms, slowing of disease progression, and prevention of disease, e.g., a therapeutically effective amount may be an amount sufficient to decrease the symptoms of a disease responsive to α-2,3-ST inhibition. In certain embodiments, a therapeutically effective amount is an amount sufficient to reduce cancer symptoms. In certain embodiments, a therapeutically effective amount is an amount sufficient to decrease the number of detectable cancerous cells in an organism. In certain embodiments, a therapeutically effective amount is an amount sufficient to detectably slow or stop the growth of a cancerous tumor. In certain embodiments, a therapeutically effective amount is an amount sufficient to shrink a cancerous tumor. In certain circumstances a patient suffering from cancer may not present symptoms of being affected. In some embodiments, a therapeutically effective amount of a chemical entity is an amount sufficient to prevent a significant increase or significantly reduce the detectable level of cancerous cells or cancer markers in the patient's blood, serum, or tissues.

"Treatment" or "treating" means any treatment of a disease in a patient, including: preventing the disease, that is, causing the at least one clinical symptom of the disease not to develop; inhibiting the disease; slowing or arresting the development of at least one clinical symptom of a disease; and relieving the disease, that is, causing the regression of at least one clinical symptom of a disease. "Treating" or "treatment" also refers to inhibiting a disease, either physically, (e.g., stabilization of a discernible symptom), physiologically, (e.g., stabilization of a physical parameter), or both, and inhibit at least one physical parameter which may not be discernible to the subject. Further, "treating" or "treatment" refers to delaying the onset of a disease or at least one clinical symptom thereof in a subject which may be exposed to or predisposed to a disease even though the subject does not yet experience or display symptoms of the disease.

"Substituted" refers to a group in which one or more hydrogen atoms are each independently replaced with the same or different substituent(s). Typical substituents include, but are not limited to, —X, —$R^{33}$, —$O^-$, =O, —$OR^{33}$, —$SR^{33}$, —$S^-$, =S, —$NR^{33}R^{34}$, =$NR^{33}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{33}$, —$OS(O_2)O^-$, —$OS(O)_2R^{33}$, —$P(O)(O^-)_2$, —$P(O)(OR^{33})(O^-)$, —$OP(O)(OR^{33})(OR^{34})$, —$C(O)R^{33}$, —$C(S)R^{33}$, —$C(O)OR^{33}$, —$C(O)NR^{33}R^{34}$, —$C(O)O^-$, —$C(S)OR^{33}$, $NR^{35}C(O)NR^{33}R^{34}$, —$NR^{35}C(S)NR^{33}R^{34}$, —$NR^{35}C(NR^{33})NR^{33}R^{34}$, —$C(NR^{33})NR^{33}R^{34}$, —$S(O)_2NR^{33}R^{34}$, —$NR^{35}S(O)_2R^{33}$, —$NR^{35}C(O)R^{33}$, and —$S(O)R^{33}$ where each X is independently a halogen; each $R^{33}$ and $R^{34}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, —$NR^{35}R^{36}$, —$C(O)R^{35}$ or —$S(O)_2R^{35}$ or optionally $R^{33}$ and $R^{34}$ together with the atom to which $R^{33}$ and $R^{34}$ are attached form one or more cycloheteroalkyl, substituted cycloheteroalkyl, heteroaryl, or substituted heteroaryl rings; and $R^{35}$ and $R^{36}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl or substituted heteroarylalkyl, or optionally $R^{35}$ and $R^{36}$ together with the nitrogen atom to which $R^{35}$ and $R^{36}$ are attached form one or more cycloheteroalkyl, substituted cycloheteroalkyl, heteroaryl, or substituted heteroaryl rings. In certain embodiments, a tertiary amine or aromatic nitrogen may be substituted with one or more oxygen atoms to form the corresponding nitrogen oxide.

In certain embodiments, substituted aryl and substituted heteroaryl include one or more of the following substituent groups: F, Cl, Br, $C_{1-3}$ alkyl, substituted alkyl, $C_{1-3}$ alkoxy, —$S(O)_2NR^{33}R^{34}$, —$NR^{33}R^{34}$, —$CF_3$, —$OCF_3$, —CN, —$NR^{35}S(O)_2R^{33}$, —$NR^{35}C(O)R^{33}$, $C_{5-10}$ aryl, substituted $C_{5-10}$ aryl, $C_{5-10}$ heteroaryl, substituted $C_{5-10}$ heteroaryl, —$C(O)OR^{33}$, —$NO_2$, —$C(O)R^{33}$, —$C(O)NR^{33}R^{34}$, —$OCHF_2$, $C_{1-3}$ acyl, —$SR^{33}$, —$S(O)_2OH$, —$S(O)_2R^{33}$, —$S(O)R^{33}$, —$C(S)R^{33}$, —$C(O)O-$, —$C(S)OR^{33}$, —$NR^{35}C(O)N^{33}R^{34}$, —$NR^{35}C(S)NR^{33}R^{34}$, and —$C(NR^{35})NR^{33}R^{34}$, $C_{3-8}$ cycloalkyl, and substituted $C_{3-8}$ cycloalkyl, $C_{3-8}$ heterocycloalkyl, and substituted $C_{3-8}$ heterocycloalkyl, as defined herein.

In certain embodiments, substituted arylalkyl, and substituted heteroarylalkyl include one or more of the following substitute groups: F, Cl, Br, $C_{1-3}$ alkyl, $C_{1-3}$ alkoxy, —$S(O)_2NR^{33}R^{34}$, —$NR^{33}R^{34}$, —$CF_3$, —$OCF_3$, CN, —$NR^{35}S(O)_2R^{33}$, —$NR^{35}C(O)R^{33}$, $C_{5-10}$ aryl, substituted alkyl, substituted $C_{5-10}$ aryl, $C_{5-10}$ heteroaryl, substituted $C_{5-10}$ heteroaryl, —$C(O)OR^{33}$, —$NO_2$, —$C(O)R^{33}$, —$C(O)NR^{33}R^{34}$, —$OCHF_2$, $C_{1-3}$ acyl, —$SR^{33}$, —$S(O)_2OH$, —$S(O)_2R^{33}$, —$S(O)R^{33}$, —$C(S)R^{33}$, —$C(O)O-$, —$C(S)OR^{33}$, —$NR^{35}C(O)NR^{33}R^{34}$, —$NR^{35}C(S)NR^{33}R^{34}$, and —$C(NR^{35})NR^{33}R^{34}$, $C_{3-8}$ cycloalkyl, and substituted $C_{3-8}$ cycloalkyl, as defined herein.

In certain embodiments, substituted alkyl includes one or more of the following substitute groups: $C_{1-3}$ alkoxy, —$NR^{33}R^{34}$, substituted $C_{5-10}$ heteroaryl, —$SR^{33}$, $C_{1-3}$ alkoxy, —$S(O)_2NR^{33}R^{34}$, CN, F, Cl, —$CF_3$, —$OCF_3$, —$NR^{35}S(O)_2R^{33}$, —$NR^{35}C(O)R^{33}$, $C_{5-10}$ aryl, substituted $C_{5-10}$ aryl, $C_{5-10}$ heteroaryl, substituted $C_{5-10}$ heteroaryl, —$C(O)OR^{33}$, —$NO_2$, —$C(O)R^{33}$, —$C(O)NR^{33}R^{34}$, —$OCHF_2$, $C_{1-3}$ acyl, —$S(O)_2OH$, —$S(O)_2R^{33}$, —$S(O)R^{33}$, —$C(S)R$, —$C(O)O^-$, —$C(S)OR^{33}$, —$NR^{35}C(O)NR^{33}R^{34}$, —$NR^{35}C(S)N^{33}R^{34}$, and —$C(NR^{35})NR^{33}R^{34}$, $C_{3-8}$ cycloalkyl, and substituted $C_{3-8}$ cycloalkyl, as defined herein.

In certain embodiments, substituted alkenyl includes one or more of the following substitute groups: $C_{1-8}$ alkyl, substituted $C_{1-8}$ alkyl, $C_{5-10}$ aryl, substituted $C_{5-10}$ aryl, $C_{5-10}$ heteroaryl, substituted $C_{5-10}$ heteroaryl, $C_{3-8}$ cycloalkyl, substituted $C_{3-8}$ cycloalkyl, cycloheteroalkylalkyl, and substituted cycloheteroalkylalkyl, as defined herein.

The term "substituted amino" refers to the group —$NHR^d$ or —$NR^dR^d$ where each $R^d$ is independently chosen from: alkyl, substituted alkyl, cycloalkyl, substituted cycloalkyl, acyl, substituted acyl, aryl, substituted aryl, heteroaryl, substituted heteroaryl, heterocycloalkyl, substituted heterocycloalkyl, alkoxycarbonyl, and sulfonyl. Representative examples include, but are not limited to, dimethylamino, methylethylamino, di-(1-methylethyl)amino, (cyclohexyl)(methyl)amino, (cyclohexyl)(ethyl)amino, (cyclohexyl)(propyl)amino, and the like.

Provided is at least one chemical entity chosen from compounds of Formula I:

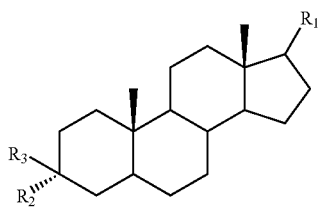

Formula I and pharmaceutically acceptable salts, solvates, chelates, non-covalent complexes, prodrugs, and mixtures thereof, wherein $R_1$ is optionally substituted alkyl; $R_2$ is chosen from hydroxy and acyloxy; $R_3$ is hydrogen, or $R_2$ and $R_3$, taken together with the carbon to which they are attached, form an oxo group; and provided that when $R_1$ is (R)-4-carboxybutan-2-yl, then $R_2$ is not hydroxy.

In certain embodiments, $R_1$ is chosen from —$CHR_4(CH_2)_n R_5$ where n is chosen from 2 and 3; $R_4$ is chosen from hydrogen and optionally substituted lower alkyl; and $R_5$ is chosen from carboxyl, aminocarbonyl, and optionally substituted heteroaryl. In certain embodiments, n is 2. In certain embodiments, n is 3. In certain embodiments, $R_4$ is chosen from hydrogen and lower alkyl. In certain embodiments, $R_4$ is lower alkyl. In certain embodiments, $R_4$ is methyl. In certain embodiments, $R_5$ is chosen from carboxyl, —(CO)—$NHR_6$, and optionally substituted triazole wherein $R_6$ is chosen from optionally substituted lower alkyl.

In certain embodiments, $R_1$ is —$CHR_4(CH_2)_n R_5$ where n is chosen from 2 and 3; $R_4$ is chosen from hydrogen and optionally substituted lower alkyl; and $R_5$ is chosen from carboxyl, —(CO)—$NHR_6$, and substituted triazole wherein the triazole ring is substituted with a group $R_7$ wherein $R_7$ is an optionally substituted lower alkyl. In certain embodiments, $R_6$ is chosen from lower alkyl substituted with one or two carboxyl groups. In certain embodiments, $R_5$ is carboxyl. In certain embodiments, $R_5$ is a substituted triazole wherein the substituent is chosen from lower alkyl substituted with one or two groups chosen from carboxyl, amino, and dialkylphosphonate, and provided that the lower alkyl group is substituted with at least one carboxyl group.

In certain embodiments, $R_1$ is chosen from:
(R)-5-hydroxypentan-2-yl;
(R)-5-(carboxymethylamino)-5-oxopentan-2-yl;
(R)-5-((S)-1,2-dicarboxyethylamino)-5-oxopentan-2-yl;
(R)-5-tert-butoxy-5-oxopentan-2-yl;
(R)-4-carboxybutan-2-yl;
(R)-5-(4-(2-hydroxyethyl)-1H-1,2,3-triazol-1-yl)pentan-2-yl;
(R)-5-(4-(2-amino-2-carboxyethyl)-1H-1,2,3-triazol-1-yl)pentan-2-yl;
(R)-5-(4-(2-carboxy-2-(diethoxyphosphoryl)ethyl)-1H-1,2,3-triazol-1-yl)pentan-2-yl;
(R)-5-(4-(2-carboxyethyl)-1H-1,2,3-triazol-1-yl)pentan-2-yl;
(R)-5-(4-(3-carboxypropyl)-1H-1,2,3-triazol-1-yl)pentan-2-yl; and
(R)-5-(diphenoxyphosphoryloxy)pentan-2-yl.

In certain embodiments, $R_2$ is chosen from hydroxy, 3-carboxypropanoyloxy; and (R)-2-amino-3-carboxypropanoyloxy.

In certain embodiments, $R_3$ is hydrogen.

In certain embodiments, $R_2$ and $R_3$ taken together with the carbon to which they are attached form an oxo group.

Further provided is a pharmaceutical composition comprising a therapeutically effective amount of the at least one chemical entity chosen from compounds of Formula I and a pharmaceutically acceptable vehicle.

Further provided is a method for inhibiting α-2,3-sialyltransferase activity comprising contacting cells expressing α-2,3-sialyltransferase with at least one chemical entity chosen from compounds of Formula I in an amount sufficient to detectably decrease the level of sialylation of glycoconjugates. In certain embodiments, the cells are cancer cells. In certain embodiments, the cancer cells are undergoing cell migration. In certain embodiments, the cell migration is associated with cancer metastasis. In certain embodiments, the cells are present in a mammal. In certain embodiments, the mammal is a human.

Further provided is a method for treating a patient having a disease responsive to inhibition of α-2,3-sialyltransferase activity comprising administering to the patient a therapeutically effective amount of at least one chemical entity chosen from compounds of Formula I. In certain embodiments, the at least one chemical entity chosen from compounds of Formula I comprises a pharmaceutical composition. In certain embodiments, the disease responsive to inhibition of α-2,3-sialyltransferase activity is cancer. In certain embodiments, the cancer is undergoing metastasis. In certain embodiments, the patient is a mammal. In certain embodiments, the mammal is a human. In certain embodiments, the method for treating a patient having a disease responsive to inhibition of α-2,3-sialyltransferase further comprises administering at least one additional therapeutic agent appropriate for effecting combination therapy.

In certain embodiments, a pharmaceutical composition can include at least one chemical entity of the present disclosure and at least one additional therapeutic agent appropriate for effecting combination therapy. Chemical entities of the present disclosure are also useful in combination with known therapeutic agents and anti-cancer agents. A person skilled in the art would be able to discern which combinations of agents would be useful based on the particular characteristics of the drugs and the cancer involved. Many chemotherapeutics are presently known in the art. Such anti-cancer agents include, but are not limited to, estrogen receptor modulators, cytostatic/cytotoxic agents, anti-proliferative agents, cell cycle checkpoint inhibitors, angiogenesis inhibitors, monoclonal antibody targeted therapeutic agents, tyrosine kinase inhibitors, serine-threonine kinase inhibitors, histone deacetylase inhibitors, heat shock protein inhibitors, and farnesyl transferase inhibitors. Chemical entities of the present disclosure are also useful in combination with radiation therapy.

Chemical entities of the present disclosure can be assayed in vitro and in vivo, for the desired therapeutic or prophylactic activity prior to therapeutic use in human subjects and other mammals. For example, in vitro assays can be used to determine whether administration of a specific compound of the present disclosure or a combination of such compounds is effective for inhibiting the activity of α-2,3-ST or treating at least one disease. In certain embodiments, the chemical entities described herein inhibit α-2,3-sialyltransferase activity in an in vitro biochemical assay with an $IC_{50}$ less then about 360 μM. In certain embodiments, the chemical entities described herein inhibit α-2,3-sialyltransferase activity in an in vitro biochemical assay with an $IC_{50}$ less then about 250 μM. In certain embodiments, the chemical entities described herein inhibit α-2,3-sialyltransferase activity in an in vitro biochemical assay with an $IC_{50}$ less then about 100 μM. In certain embodiments, the chemical entities described herein inhibits α-2,3-sialyltransferase activity in an in vitro biochemical assay with an $IC_{50}$ less then about 25 μM.

Chemical entities of the present disclosure can also be demonstrated to be effective and safe using animal model systems. A therapeutically effective dose of at least one chemical entity of the present disclosure can, in certain embodiments, provide therapeutic benefit without causing substantial toxicity. Toxicity of the chemical entities of the present disclosure can be determined using standard pharmaceutical procedures and can be readily ascertained by the skilled artisan. The dose ratio between toxic and therapeutic effect is the therapeutic index. Chemical entities of the present disclosure may exhibit high therapeutic indices in treating diseases and disorders. The dosage of a compound of the present disclosure can be within a range of circulating concentrations that include an effective dose with little or no toxicity.

When employed as pharmaceuticals, chemical entities of the present disclosure can be administered in the form of pharmaceutical compositions. Such compositions can be prepared in any manner known in the pharmaceutical art and can comprise at least one chemical entity of the present disclosure. In the treatment of disease, chemical entities of the present disclosure can be administered in a therapeutically effective amount. It will be understood, however, that the amount of the compound administered will be determined by a physician in light of the relevant circumstances, including the condition to be treated; the chosen route of administration; the actual compound administered; the age, weight, and response of the individual subject; the severity of the subject's symptoms; and the like.

Pharmaceutical compositions of the present disclosure can comprise a therapeutically effective amount of at least one chemical entity of the present disclosure, and at least one pharmaceutically acceptable vehicle. Pharmaceutical compositions of the present disclosure can additionally comprise at least one additional compound that enhances the therapeutic efficacy of one or more chemical entities of the present disclosure. For example, but without being limited by theory, such compounds can enhance the therapeutic efficacy of chemical entities of the present disclosure by effectively increasing the plasma concentration of the compounds; decrease the degradation of the chemical entities of the present disclosure prior to administration or during transport to the plasma, or within the plasma; and increase the plasma concentration by increasing the absorption of compounds in the gastrointestinal tract. Pharmaceutical compositions of the present disclosure can also include additional therapeutic agents that are normally administered to treat a disease or disorder to provide combination therapy as described above.

Some embodiments of the present disclosure are directed to compositions that contain, as the active ingredient, of one or more chemical entities of the present disclosure associated with pharmaceutically acceptable excipients. In making certain compositions of the present disclosure, the active ingredient can be mixed with an excipient, diluted by an excipient, or enclosed within such a carrier that can be in the form of a capsule, sachet, paper, or other such container. When the excipient serves as a diluent, the excipient can be a solid, semi-solid, or liquid material, which acts as a vehicle (e.g. a carrier) for the active ingredient. Thus, for example, the compositions can be in the form of tablets, pills, powders, lozenges, sachets, cachets, elixirs, suspensions, emulsions, solutions, soft gelatin capsules, hard gelatin capsules, and syrups containing, for example, from about 1% to about 90% by weight of at least one chemical entity of the present disclosure.

In preparing a composition, it can be necessary to mill active compound to provide the appropriate particle size prior to combining with other ingredients. If the active compound is insoluble, the active component ordinarily can be milled to a particle size of less than 200 mesh. If the active compound is water soluble, the particle size can be adjusted by milling to provide a uniform distribution in the formulation, e.g. 40 mesh.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, modified cyclodextrins, cellulose, water, syrup, and methyl cellulose. Some compositions can additionally include: lubricating agents such as talc, magnesium stearate, and mineral oil; wetting agents; emulsifying and suspending agents; preserving agents such as methyl and propylhydroxy-benzoates; sweetening agents; and flavoring agents. Compositions of the present disclosure can be formulated so as to provide quick, sustained, or delayed release of the active ingredient after administration to the subject by employing procedures known in the art.

Some compositions of the present disclosure can be formulated in unit dosage form, each dosage containing, for example, about 0.1 mg to about 2 g of the active ingredient. As used herein, "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, diluent, carrier, and adjuvant. In certain embodiments, compositions of the present disclosure can be formulated in multiple dosage forms. The amount of the chemical entities of the present disclosure that can be combined with other materials and therapeutic agents to produce compositions of the present disclosure in a single dosage form will vary depending upon the disease, the subject, and the particular mode of administration.

For preparing solid compositions such as tablets, the principal active ingredient can be mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills, and capsules. The solid preformulation can then subdivided into unit dosage forms of the type described above containing from, for example, about 0.1 mg to about 2 g of the therapeutically effective compound of the present disclosure.

The tablets or pills comprising certain compositions of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials include a number of polymeric acids and mixtures of polymeric acids with such materials as shellac, cetyl alcohol, and cellulose acetate.

The liquid forms in which the compositions of the present disclosure may be incorporated for administration orally, by injection, and the like include aqueous solutions, suitably flavored syrups, aqueous or oil suspensions, and flavored emulsions with edible oils such as cottonseed oil, sesame oil, coconut oil, and peanut oil, as well as elixirs and similar pharmaceutical vehicles.

In certain embodiments, pharmaceutical compositions of the present disclosure may be administered orally, parenterally, by inhalation spray, topically, rectally, nasally, buccally, vaginally, via an implanted reservoir, or by any other appropriate route. Pharmaceutical compositions of the present disclosure can contain one or more pharmaceutically acceptable vehicles. In some embodiments, the pH of the formulation can be adjusted with pharmaceutically acceptable acids, bases or buffers to enhance the stability of the formulated compound or the delivery form. The term parenteral as used herein includes subcutaneous, intra-ocular, intracutaneous, intravenous, intraperitoneal, intramuscular, intra-articular, intraportal, intra-arterial, interasynovial, intrasternal, interathecal, intralesional, intracerebral (intra-parenchymal), intracerebroventricular, and intracranial injection or infusion techniques. In certain embodiments, the compositions can be administered by bolus injection or continuously by infusion, or by an implantation device.

In certain embodiments, compounds disclosed herein can be delivered orally. In certain embodiments, a compound of the present disclosure, with or without at least one additional therapeutic agent, can be formulated with or without carriers customarily used in the compounding of solid dosage forms such as tablets and capsules. In other embodiments, a capsule may be designed to release the active portion of the formulation in the region of the gastrointestinal tract where bioavailability can be maximized and pre-systemic degradation minimized. In certain embodiments, at least one additional agent can be included in the formulation to facilitate absorption of the compound of the present disclosure and any additional therapeutic agents into the systemic circulation. In certain embodiments, diluents, flavorings, low melting point waxes, vegetable oils, lubricants, suspending agents, tablet disintegrating agents, and binders can be employed. Suitable dosage ranges for oral administration can depend on the potency of the compounds, but generally can range from about 0.1 mg to about 20 mg of a compound per kilogram of body weight.

In certain embodiments, pharmaceutical compositions of the present disclosure can be selected for parenteral delivery. In certain embodiments, when parenteral administration is contemplated, a therapeutic composition can be in the form of a pyrogen-free, parenterally acceptable aqueous solution comprising at least one chemical entity of the present disclosure, with or without additional therapeutic agents, in a pharmaceutically acceptable vehicle. In other embodiments, a vehicle for parenteral injection can be sterile distilled water in which at least one chemical entity of the present disclosure, with or without at least one additional therapeutic agent, is formulated as a sterile, isotonic solution, properly preserved. In certain embodiments, the pharmaceutical composition can include encapsulation of at least one chemical entity of the present disclosure with an agent, such as injectable microspheres, bio-erodible particles, polymeric compounds such as polyacetic acid or polyglycolic acid, beads or liposomes, that can provide the controlled or sustained release of the compound of the present disclosure which can then be delivered via a depot injection. In certain embodiments, implantable drug delivery devices can be used to introduce a compound of the present disclosure to the plasma of a subject, within a target organ, and to a specific site within the subject's body.

In certain embodiments, a pharmaceutical composition can be formulated for inhalation. In certain embodiments, a compound of the present disclosure, with or without at least one additional therapeutic agent, can be formulated as a dry powder for inhalation. In certain embodiments, an inhalation solution comprising at least one chemical compound of the present disclosure, with or without at least one additional therapeutic agent, can be formulated with a propellant for aerosol delivery. In other embodiments, solutions can be nebulized. In certain embodiments, solutions, powders, or dry films of chemical entities of the present disclosure can be aerosolized or vaporized, for example, for pulmonary delivery.

In certain embodiments, a pharmaceutical composition can be formulated for topical administration. Topical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like. Other materials suitable for use in topical carriers include, for example, emollients, solvents, humectants, thickeners, and powders.

In certain embodiments, the composition can be administered locally via implantation of a membrane, sponge or another appropriate material onto which the desired compound of the present disclosure has been absorbed or encapsulated. In certain embodiments, where an implantation device is used, the device can be implanted into any suitable tissue or organ, and delivery of the desired molecule via diffusion, timed-release bolus, or continuous administration.

A pharmaceutical composition of the present disclose includes any pharmaceutically acceptable salt, ester, salt of an ester or other derivative and prodrugs of a compound of the present disclosure that, upon administration to a recipient, is capable of providing, either directly or indirectly, a compound of the present disclosure or an inhibitory active metabolite or residue thereof. Examples of derivatives and prodrugs include, but are not limited to, acetate, formate, benzoate, and like derivatives of functional groups (such as alcohol or amine groups) in the compounds of the present disclosure. Derivates and prodrugs include those that increase the bioavailability of the chemical entities of the present disclosure when such compounds are administered to a mammal, e.g., by allowing an orally administered compound to be more readily absorbed into the blood, or which enhance delivery of the parent compound to a biological compartment, e.g., the brain or lymphatic system, relative to the parent species.

In certain embodiments, a pharmaceutical composition of the present disclosure can contain formulation materials for modifying, maintaining, and preserving, for example, the pH, osmolarity, viscosity, clarity, color, isotonicity, odor, sterility, stability, rate of dissolution and release, adsorption and penetration of the composition. In certain embodiments, suitable formulation materials include, but are not limited to, amino acids such as glycine, glutamine, asparagine, arginine and lysine; antimicrobials; antioxidants such as ascorbic acid, sodium sulfite, and sodium hydrogen-sulfite; buffers such as borate, bicarbonate, Tris-HCl, citrates, phosphates and other organic acids; bulking agents such as mannitol and glycine; chelating agents such as ethylenediamine tetraacetic acid (EDTA); complexing agents such as caffeine, polyvinylpyrrolidone, beta-cyclodextrin, hydroxypropyl-beta-cyclodextrin, and sulfobutyl ether β-cyclodextrin; fillers; monosaccharides; disaccharides; and other carbohydrates such as glucose, mannose, and dextrins; proteins such as serum albumin, gelatin and immunoglobulins; coloring, flavoring and diluting agents; emulsifying agents; hydrophilic polymers such as polyvinylpyrrolidone; low molecular weight polypeptides; salt-forming counterions such as sodium; preservatives such as benzalkonium chloride, benzoic acid, salicylic acid, thimerosal, phenethyl alcohol, methylparaben, propylparaben, chlorhexidine, sorbic acid and hydrogen peroxide; solvents such as glycerin, propylene glycol and polyethylene glycol; sugar alcohols such as mannitol and sorbitol; suspending agents; surfactants and wetting agents such as pluronics, PEG, sorbitan esters, polysorbates such as polysorbate 20, polysorbate 80, triton, tromethamine, lecithin, cholesterol, tyloxapal; stability enhancing agents such as sucrose and sorbitol; tonicity enhancing agents such as alkali metal halides, such as sodium and potassium chloride, mannitol, sorbitol; delivery vehicles; diluents; excipients, and pharmaceutical adjuvants (Remington's Pharmaceutical Sciences, 18th Edition, A. R. Gennaro, ed., Mack Publishing Company (1990)).

In certain embodiments, the optimal pharmaceutical composition can be determined by one skilled in the art depending upon, for example the intended route of administration, delivery format, and desired dosage. See, for example, Remington's Pharmaceutical Sciences, supra. In certain embodiments, such compositions may influence the physical state, stability, rate of in vivo release, and rate of in vivo clearance of the chemical entities of the present disclosure. Appropriate dosages can be in the range of about 25 to about 500 mg/day and the dose of compounds administered can be adjusted to provide an equivalent molar quantity of compound in the plasma of a subject. A dosage can be delivered in a composition by a single administration, by multiple applications, by sustained release, by controlled sustained release, or any other appropriate intervals and rates of release. Dosage ranges and administration can be readily determined by methods known to those skilled in the art. In certain embodiments, the frequency of dosing will take into account the pharmacokinetic parameters of the chemical entities of the present disclosure and any additional therapeutic agents in the pharmaceutical composition used. In certain embodiments, a clinician can administer the composition until a dosage is reached that achieves the desired effect. The composition can be administered as a single dose, or as two or more doses, which may or may not contain the same amount of the therapeutically active compound time, or as a continuous infusion via an implantation device or catheter. Further refinement of an appropriate dosage can be routinely made by those of ordinary skill in the art. For example, therapeutically effective amounts and regimens can be determined through use of appropriate dose-response data.

The quantity of a compound of the present disclosure required for the treatment of a particular condition can vary depending on the compound, and the condition of the subject to be treated. In general, daily dosages can range from about 100 ng/kg to about 100 mg/kg, e.g., 0.01 mg/kg to 40 mg/kg body weight, for oral or buccal administration; 0.001 mg/kg to 20 mg/kg body weight, for parenteral administration; and from 0.05 mg to 1,000 mg for nasal administration or administration by inhalation or insufflation.

In certain embodiments, it can be desirable to use a pharmaceutical composition comprising a compound of the present disclosure, with or without at least one additional therapeutic agent, in an ex vivo manner. For example, cells, tissues, or organs that have been removed from a subject are exposed to a pharmaceutical composition comprising a compound of the present disclosure, with or without at least one additional therapeutic agent, after which the cells, tissues, or organs are subsequently implanted back into the subject.

The compositions of the present disclosure can, if desired, be presented in a pack or dispenser device that can contain one or more unit dosage forms containing the active ingredient. The pack or dispensing device can be accompanied by instructions for administration. Such packaged formulations include a pharmaceutical composition comprising at least one chemical entity of the present disclosure, and instructions for using the composition to treat a mammal (typically a human patient). Also provided is prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

Embodiments of the present disclosure can be further defined by reference to the following examples, which describe in detail preparation of chemical entities of the present disclosure and assays for using chemical entities of the present disclosure. It will be apparent to those skilled in the art that many modifications, both to materials and methods, may be practiced without departing from the scope of the present disclosure.

EXAMPLES

Example 1

Novel Membrane-Permeable Lithocholic Acid Analogues that Inhibit α-2,3-Sialyltransferase This example describes the synthesis of lithocholic acid analogues that employ a steroidal moiety to improve their permeability across membranes and that demonstrate non-competitive inhibition of α-2,3-sialyltransferase (α-2,3-ST) in the presence of the transition-state analogue cytidine monophosphate-N-acetylneuraminic acid (CMP-Neu5Ac). Soyasaponin I (compound 1), a rigid pentacyclic system with a trisaccharide from soybean saponin, has been identified as a new type of ST inhibitor that shows significant inhibition ($K_i$=2.1 mM) of α-2,3-ST in vivo (Hsu et al., *Gynecol. Oncol.*, 2005, 96:415). To identify steroid-related compounds that inhibit α-2,3-ST activity, different steroid compounds were screened and lithocholic acid (compound 3) was identified as a potent inhibitor with an $IC_{50}$ value of 21 mM. Reaction Scheme 1 shows the rigid pentacyclic system and trisaccharide of soyasaponin I (compound 1) and the main skeleton of lithocholic acid (compound 3). Compound 3 is formed from compound 1 by cleaving bonds (a) and (b) followed by conversion of the D-ring into a 5-membered ring, and oxidization of the terminal alcohol into carboxylic acid.

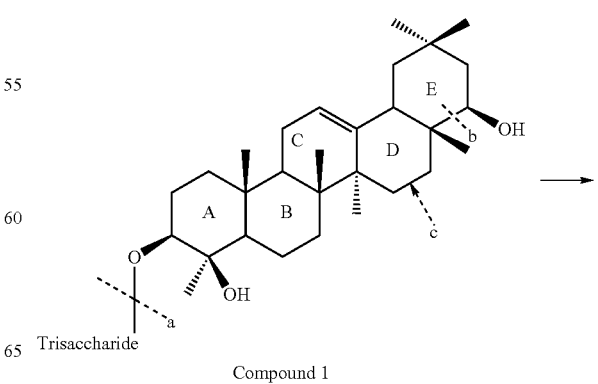

Reaction Scheme 1

Compound 1

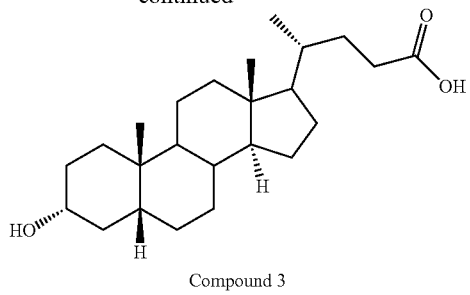

Compound 3

Synthesis of lithocholic acid analogues (compounds 7-22) was then undertaken to identify novel membrane-permeable inhibitors of α-2,3-ST. Compound synthesis was carried out with the following materials according the following general procedures. All chemicals and buffers were purchased from Sigma, Aldrich, or Acros Organics; and all amino acids were purchased from Advanced Chemtech. CMP-Neu5Ac was synthesized starting with sialic acid (Traving & Schauer, *Cell. Mol. Life Sci.*, 1998, 54:1330; Schwarzkopf et al., *Proc. Natl. Acad. Sci. USA*, 2002, 99:5267). Synthesis of lactose acceptor was achieved as described in Harduin-Lepers et al., *Biochimie*, 2001, 83:727. Rat liver α-2,3-ST was obtained from CalBiochem at a concentration of 3.7 mU/μL, stored at −80° C., and used within one week. Melting points (m.p.) were recorded with a capillary melting point apparatus (Electrothermal MEL-TEMP); FT-IR spectra were recorded with Perkin Elmer FT-IR Spectrometer (Paragon 1000) in KBr pellets; $^1$H and $^{13}$C NMR spectra were recorded with Bruker AMX400 or 500 MHz instruments. Proton chemical shifts (δ) are reported in parts per million (ppm) relative to the methine singlet at 7.24 ppm for the residual CHCl$_3$ in the deuteriochloroform, or the methyl pentet at 3.30 ppm for the residual CHD$_2$OD in the methanol-d$_4$. Carbon chemical shifts are reported in ppm relative to the internal $^{13}$C signals in CDCl$_3$ (77.0 ppm) and CD$_3$OD-d$_4$ (49.0 ppm). Mass spectra were obtained with a FAB JMS-700 double focusing mass spectrometer (JEOL, Tokyo, Japan), MALDI Voyager DE-PRO (Applied Biosystem Houston, USA), and ESI Finnigan LCQ mass spectrometer (Thermo Finnigan, San Jose, Calif., United States) in negative mode. The peptide compounds were purified by reversed phase HPLC (Waters 2695 System with a 996 PDA detector) using Vydac 214TP510 C4 (1 cm×25 cm) column to a purity greater than 95% as determined by analytical HPLC. The separation procedure was performed using H$_2$O/0.1% trifluoroacetic acid (TFA) (A) and CH$_3$CN/0.05% TFA (B) as eluents.

The general procedure for the phosphorylation of steroid was as follows: Tris(p-nitrophenyl)phosphate (1.30 mmol) and steroid (1.43 mmol) were dissolved in dichloromethane (20 cm$^3$). 7,11-diazabicyclo[5.4.0]undec-11-ene (1.82 mmol) was added and the reaction was stirred at room temperature for 12 hours. The reaction mixture was washed by saturated aqueous sodium bicarbonate several times, and the organic extracts were dried by Na$_2$SO$_4$, filtered, and concentrated. The resulting pale yellow solid was dissolved in dichloromethane (16 cm$^3$); methanol (13.00 mmol, 0.54 cm$^3$) and 7,11-diazabicyclo[5.4.0]undec-11-ene (6.5 mmol) were added; and the reaction was stirred at room temperature for 15 hours. The mixture was washed by saturated aqueous sodium bicarbonate several times, and the organic extracts were dried by Na$_2$SO$_4$, filtered, and concentrated. The residues were purified by silica gel using ethyl acetate and hexane as eluents to afford the product.

The general procedure for deprotection of the methoxy of steroidal phosphate was as follows: Phophorylated steroidal compound (0.25 mmol) was dissolved in dichloromethane (1.50 cm$^3$), then bromotrimethylsilane (0.13 cm$^3$, 1.00 mmol) was added, and the reaction was stirred at room temperature for 30 minutes. The reaction was quenched by adding saturated aqueous sodium bicarbonate and the organic solvent was removed by rotary evaporation. The resulting mixture was precipitated by dichloromethane and hexane, filtered, concentrated, and dried under vacuum system to afford the product.

The general procedure for coupling of succinic anhydride and steroidis was as follows: Steroid (0.69 mmol) was dissolved in pyridine (10 cm$^3$), succinic anhydride (2.07 mmol) was added followed by 4-(dimethylamino)pyridine (0.69 mmol), and the solution was refluxed for 15 hours. After removal of pyridine by vacuum pump, the mixture was dissolved in dichloromethane and washed with saturated sodium bicarbonate and 6% HCl. The extracts were dried and evaporated to yield the crude product as sticky oil, which was purified by column chromatography on silica gel using ethyl acetate and hexane to give the product.

The general procedure for esterification of 3-hydroxy lithocholic acid and amino acid was as follows: To a solution of the protected lithocholic acid (0.35 mmol), amino acid (0.45 mmol) and 4-(dimethylamino)pyridine (0.10 mmol) in dichloromethane (8 cm$^3$) was added a solution of dicyclohexylcarbodiimide in dichloromethane (2 cm$^3$). The reaction was stirred at room temperature for 30 minutes and the solvent was removed by rotary evaporation. The resulting residue was purified by column chromatography on silica gel using ethyl acetate and hexane to afford the product.

The general procedure for peptide bond formation of lithocholic acid and amino acid was as follows: To a solution of lithocholic acid (1.33 mmol) and amino acid (1.39 mmol) in dimethylformamide (DMF) (5 cm$^3$) was added diisopropylethylamine (3.99 mmol) and 2-(1H-benzotriazole-1-yl)-1,1,3,3-tetramethyluronium hexafluorophosphate (HBTU) (1.46 mmol). The reaction was stirred at room temperature for one hour and the solvent was removed by vacuum. The mixture was dissolved in dichloromethane (50 cm$^3$) and washed twice with water (50 cm$^3$). The extracts were dried and evaporated to afford the crude product as a sticky oil, which was purified by column chromatography on silica gel using ethyl acetate and hexane to afford the product.

The general procedure for deprotection of Fmoc group was as follows: To a solution of the Fmoc-protected steroidal compound (0.15 mmol) in dichloromethane (5 cm$^3$) was added neat 7,11-diazabicyclo[5.4.0]undec-11-ene (0.15 mmol) dropwise. The reaction was stirred at room temperature for 30 minutes, and the reaction solvent was removed by rotary evaporation to yield the crude product as an oil, from which the product was purified by flash column using ethyl acetate and hexane.

The general procedure for deprotection of Boc and tBu groups was as follows: A solution of protected compound (0.15 mmol) in TFA (2 cm$^3$) was treated at room temperature with 2% water (0.04 cm$^3$). After 30 minutes, the reaction solvent was removed by rotary evaporation, and then the resulting mixture was neutralized with saturated sodium bicarbonate and purified by reverse phase HPLC to afford the pure product.

The general procedure for reduction of the methyl ester group was as follows: The steroidal methyl ester (0.56 mmol) was dissolved in tetrahydrofuran (1.6 cm$^3$), to which a solution of lithium aluminium hydride (1.13 mmol) in tetrahydrofuran (0.6 cm$^3$) was added cautiously dropwise over 10 minutes at 0° C. The reaction mixture was stirred at room temperature for 10 minutes and quenched by 6% HCl. The mixture was then filtered and solvent removed by rotary evaporation. The resulting solid was purified by column chromatography on silica gel using ethyl acetate and hexane to give the final product.

The general procedure for synthesis of diphenylphosphate steroid was as follows: To a solution of primary steroidal alcohol (2.02 mmol) in tetrahydrofuran (12 cm³) containing diphenylphosphoryl azide (3.03 mmol) was added neat 7,11-diazabicyclo[5.4.0]undec-11-ene (5.05 mmol) dropwise. The reaction was stirred at room temperature for 10 hours and quenched by 6% HCl. The solvent was removed by rotary evaporation, and the mixture was extracted by water and dichloromethane. The extracts were then dried and evaporated under reduced pressure to give the crude product, which was then purified to the final product by flash column using ethyl acetate and hexane.

The general procedure for synthesis of steroidal azide was as follows: Diphenylphosphate steroid (0.841 mmol) was dissolved in 1,4-dioxane (15 cm³) to which sodium azide (4.2 mmol), tetrabutyl ammonium iodide (0.084 mmol) and 15-crown-5 (0.1 cm³) were added. The mixture was heated under reflux in an atmosphere of nitrogen overnight. After the mixture cooled, the solvent was removed by rotary evaporation, and the residue was extracted by water and dichloromethane. The extracts were dried and evaporated under reduced pressure to give the crude product as a powder, which was purified by column chromatography on silica gel using ethyl acetate and hexane to obtain the product.

The general procedure for synthesis of steroidal 1,4-disubstituted 1,2,3-triazole was as follows: Steroidal azide (0.26 mmol) and alkyne (0.283 mmol) were dissolved in tetrahydrofuran and water (4 cm³, 1:1). Copper sulfate (catalytic amount) and sodium ascorbate (catalytic amount) were added and the reaction was stirred at room temperature for 3 hours. The solvent was removed by rotary evaporation, and the mixture was extracted by water and dichloromethane. The extracts were dried and evaporated under reduced pressure to give the crude powder, which was purified by column chromatography on silica gel using ethyl acetate and methanol to afford the product.

The general procedure for the click chemistry concept approach was as follows: Various 1,4-disubstituted 1,2,3-triazoles were generated by copper(I)-catalyzed ligation of an azide intermediate with the appropriate alkyne according to the protocol of Rostovtsev et al., (2002) Angew. Chem., Int. Ed., 41:2596.

Synthesis of Compound 7: (3R,5R,10S,13R,14S)-17-((R)-5-hydroxypentan-2-yl)-10,13-dimethyl-hexadecahydro-1H-cyclopenta[a]phenanthren-3-ol

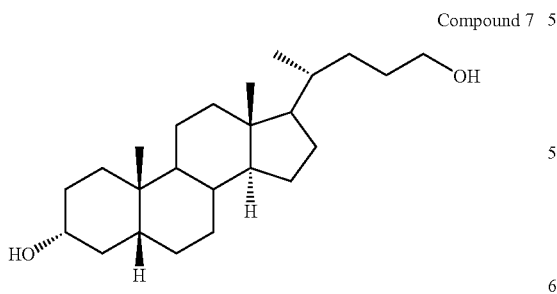

Compound 7

Compound 7 was synthesized from lithocholic acid (compound 3) in two steps as shown in Reaction Scheme 2. In step (a) compound 3 was treated with Amberlite IR120/MeOH at 80° C. for 12 hours, after which step (b), LAH, THF at 0° C. to room temperature for 10 minutes, was used to reduce the resulting methyl ester.

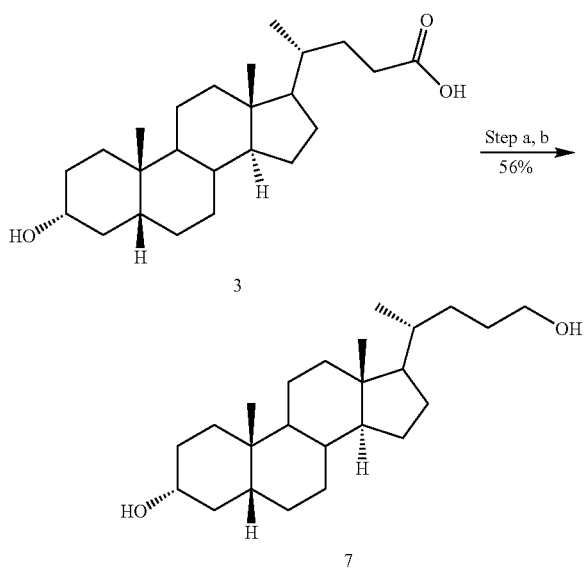

Reaction Scheme 2

Synthesis of Compound 8: (R)-4-((3R,5R,10S,13R,14S)-3-hydroxy-10,13-dimethyl-hexadecahydro-1H-cyclopenta[a]phenanthren-17-yl)pentyl diphenyl phosphonate

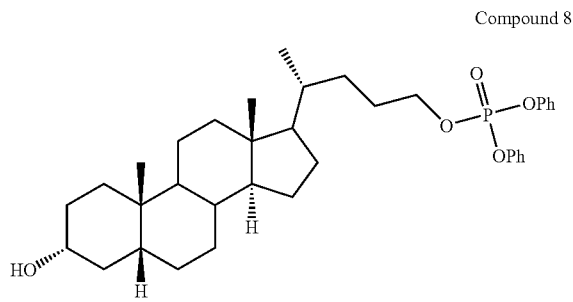 [SMILES: C[C@H](CCCOP(=O)(Oc1ccccc1)Oc1ccccc1)C1CC[C@H]2C3CC[C@@H]4C[C@H](O)CC[C@]4(C)C3CC[C@]12C]

Compound 8

Compound 8 was synthesized from compound 7 according to Reaction Scheme 3. Specifically, in step (c) the hydroxyl group of compound 7 was converted to a diphenylphosphate group in the presence of diphenyl phosphorylazide (DPPA) and DBU at room temperature for 10 hours.

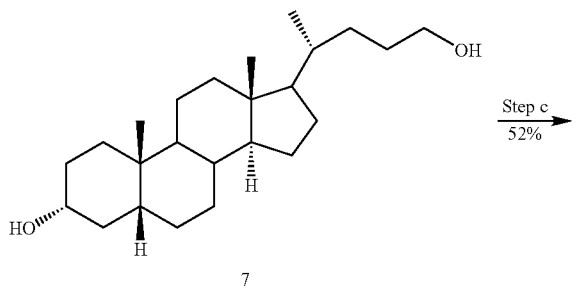

Reaction Scheme 3

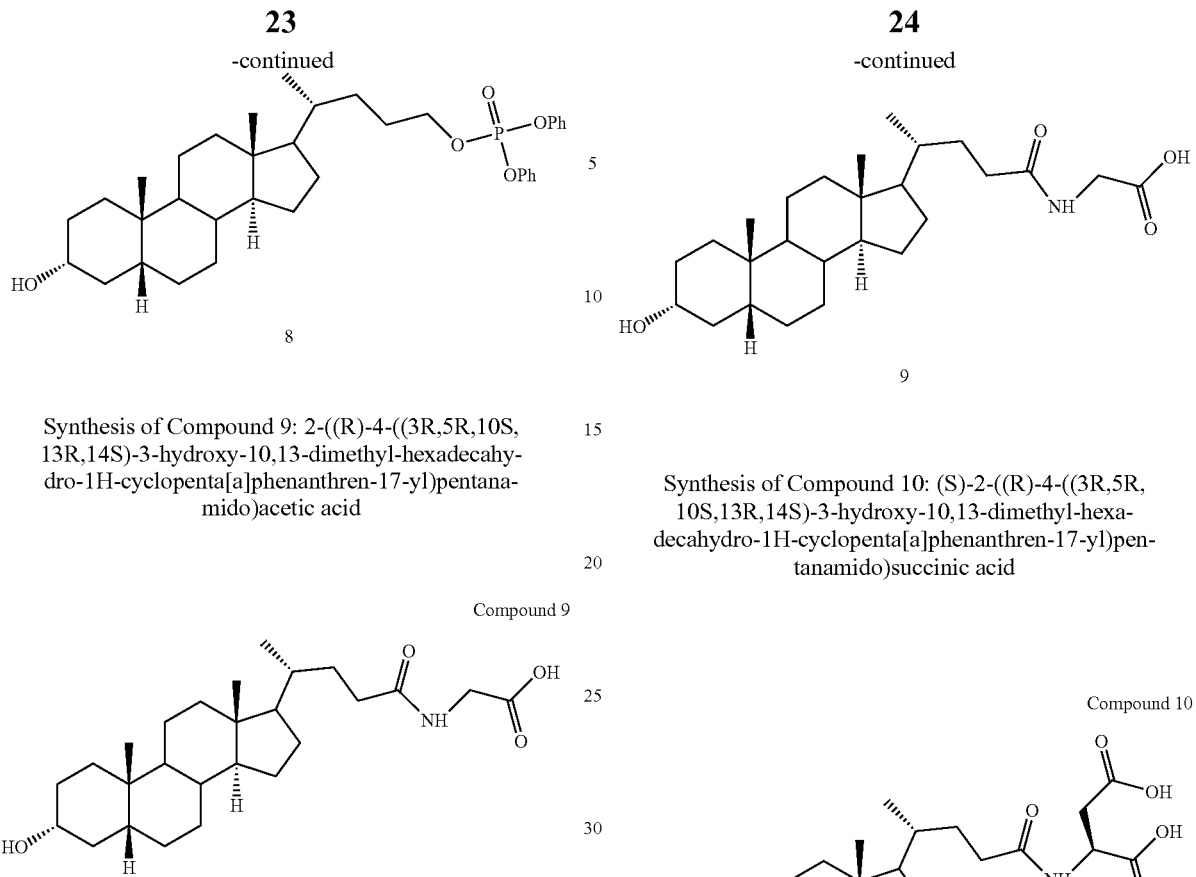

Synthesis of Compound 9: 2-((R)-4-((3R,5R,10S,13R,14S)-3-hydroxy-10,13-dimethyl-hexadecahydro-1H-cyclopenta[a]phenanthren-17-yl)pentanamido)acetic acid Compound 9 was synthesized from compound 3 according to Reaction Scheme 4. Condensation of 3 and the protected amino acid H-Gly-OBut was performed in step (e) using 2-(1H-benzotriazol-1-yl)-1,1,3,3-tetramethyluronium hexafluorophosphate (HBTU)/diisopropylethylamine (DIPEA) as coupling agent in N,N-dimethylformamide (DMF) at room temperature for 30 minutes to give the protected conjugated intermediate. Compound 9 was obtained after removal of the tBu group in step (f) using TFA, DCM at room temperature for 1 hour.

Synthesis of Compound 10: (S)-2-((R)-4-((3R,5R,10S,13R,14S)-3-hydroxy-10,13-dimethyl-hexadecahydro-1H-cyclopenta[a]phenanthren-17-yl)pentanamido)succinic acid Compound 10 was synthesized from compound 3 according to Reaction Scheme 5. Condensation of 3 and the protected amino acid L-H-Asp(OBut)-OBut was performed in step (e) using 2-(1H-benzotriazol-1-yl)-1,1,3,3-tetramethyluronium hexafluorophosphate (HBTU)/diisopropylethylamine (DIPEA) as coupling agent in N,N-dimethylformamide (DMF) at room temperature for 30 minutes to give the protected conjugated intermediate. Compound 10 was obtained after removal of the tBu group in step (f) using TFA, DCM at room temperature for 1 hour.

Reaction Scheme 4

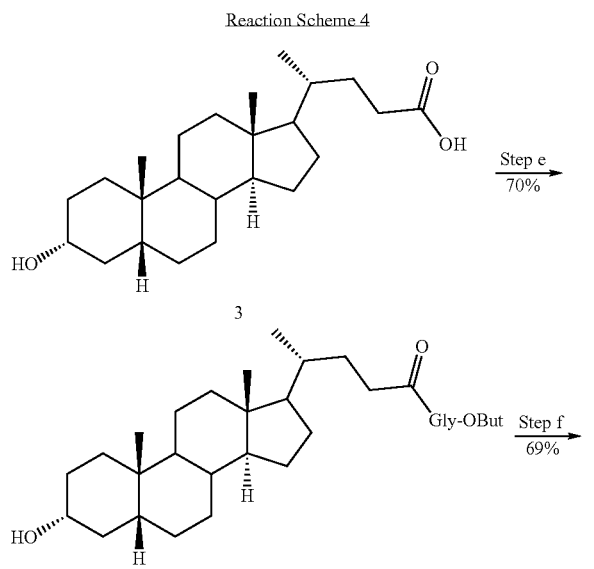

Reaction Scheme 5

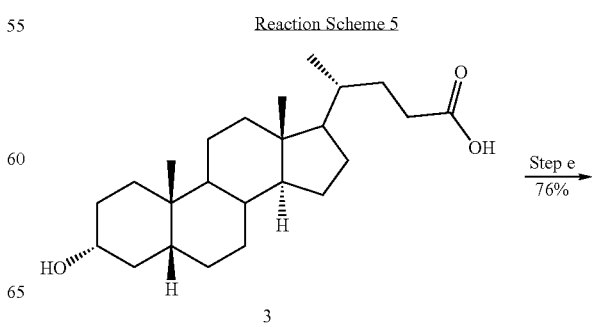

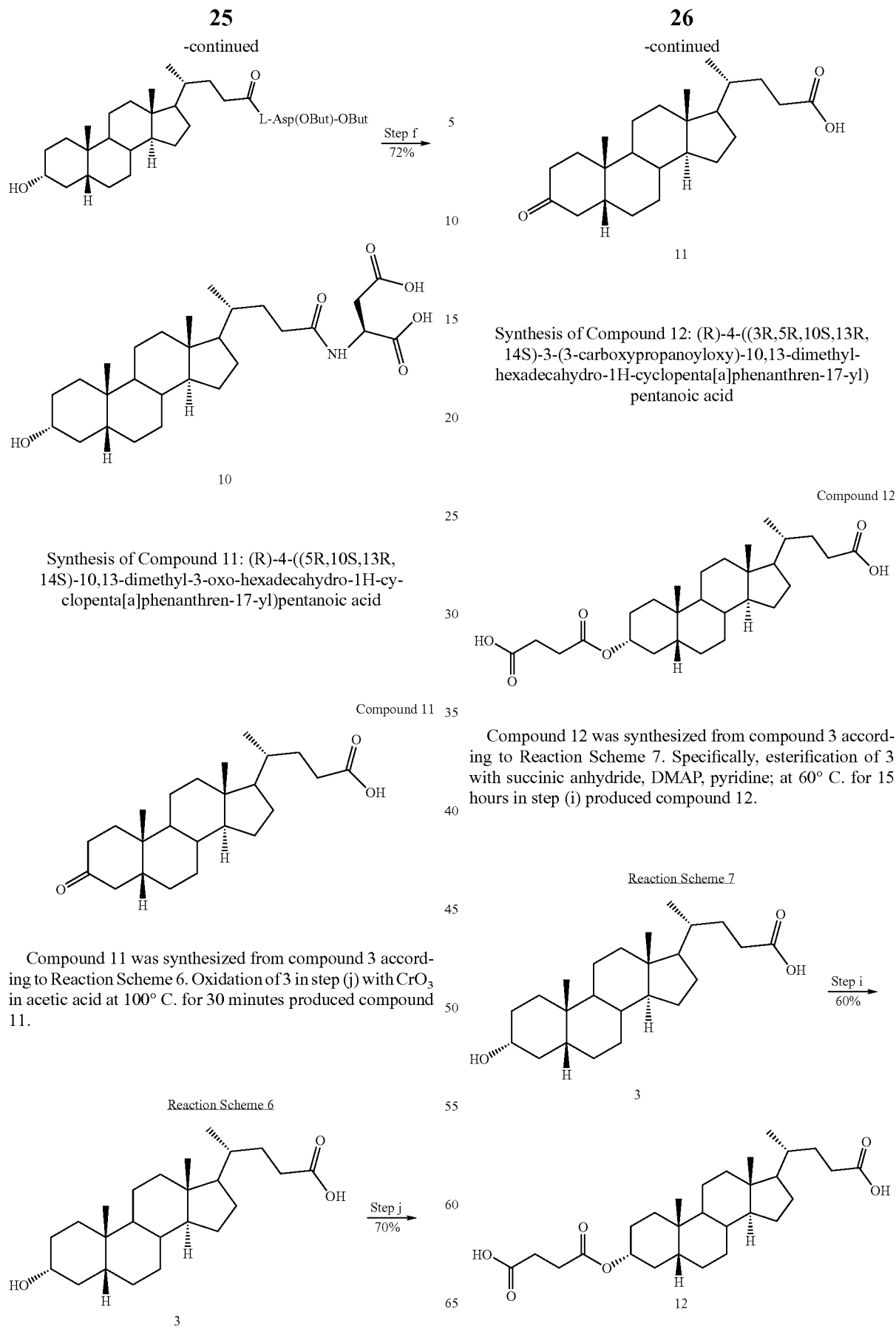

Synthesis of Compound 11: (R)-4-((5R,10S,13R,14S)-10,13-dimethyl-3-oxo-hexadecahydro-1H-cyclopenta[a]phenanthren-17-yl)pentanoic acid Compound 11 was synthesized from compound 3 according to Reaction Scheme 6. Oxidation of 3 in step (j) with $CrO_3$ in acetic acid at 100° C. for 30 minutes produced compound 11.

Synthesis of Compound 12: (R)-4-((3R,5R,10S,13R,14S)-3-(3-carboxypropanoyloxy)-10,13-dimethyl-hexadecahydro-1H-cyclopenta[a]phenanthren-17-yl)pentanoic acid Compound 12 was synthesized from compound 3 according to Reaction Scheme 7. Specifically, esterification of 3 with succinic anhydride, DMAP, pyridine; at 60° C. for 15 hours in step (i) produced compound 12.

Synthesis of Compound 13: (R)-4-((3R,5R,10S,13R,14S)-3-((S)-2-amino-3-carboxypropanoyloxy)-10,13-dimethyl-hexadecahydro-1H-cyclopenta[a]phenanthren-17-yl)pentanoic acid Compound 13

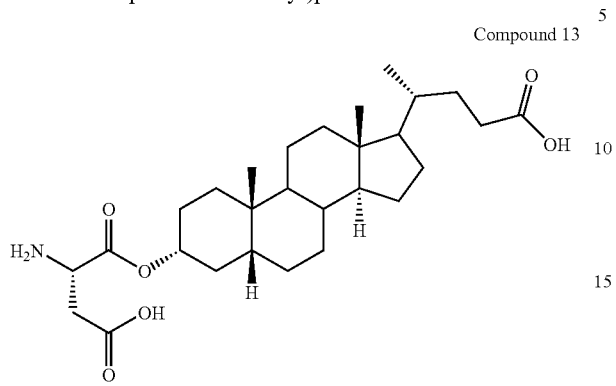

Compound 13 was synthesized from compound 3 according to Reaction Scheme 8. To prepare compound 13, the hydroxyl group of 3 was transformed to an acetyl group in step (k) using acetic anhydride, pyridine, at room temperature for 5 hours followed by an esterification step (step l) with t-BuOH, DMAP, DCC, DCM; at room temperature for 30 minutes to give the first intermediate in Reaction Scheme 8. Deacylation in step (m) using NaOCH$_3$, MeOH at room temperature for 2 hours produced the second intermediate, which was converted to the desired product 13 by dicyclohexylcarbodiimide (DCC)-promoted coupling followed by deprotection of the Fmoc, Boc, and tBu groups in three steps: (n) Fmoc-L-Asp(OBut)-OH, DMAP, DCC, DCM at room temperature for 30 minutes; (o) DBU, DCM at room temperature for 1 hour; and (h) TFA, 2% H$_2$O at room temperature for 1 hour.

Reaction Scheme 8

Synthesis of Compound 14: 4-((3R,5R,10S,13R,14S)-17-((R)-5-tert-butoxy-5-oxopentan-2-yl)-10,13-dimethyl-hexadecahydro-1H-cyclopenta[a]phenanthren-3-yloxy)-4-oxobutanoic acid Compound 14

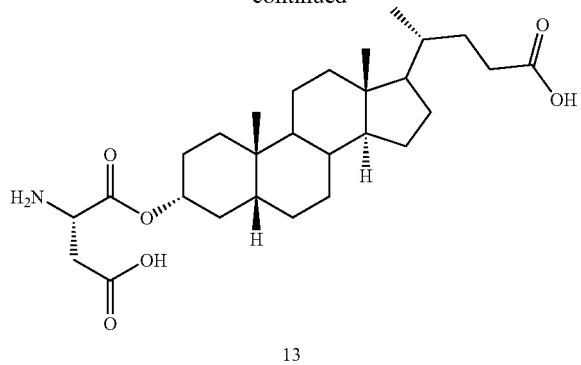

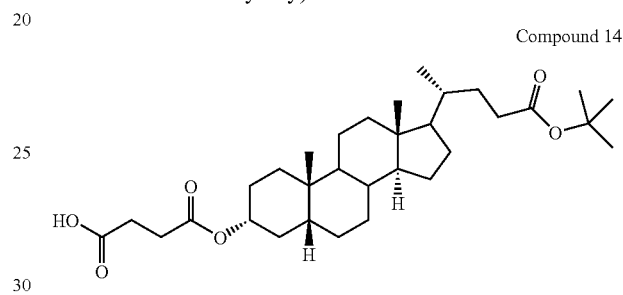

Compound 14 was synthesized from compound 3 according to Reaction Scheme 9. To prepare compound 14, the hydroxyl group of 3 was transformed to an acetyl group in step (k) using acetic anhydride, pyridine, at room temperature for 5 hours followed by an esterification step (step l) with t-BuOH, DMAP, DCC, DCM; at room temperature for 30 minutes to give the first intermediate in Reaction Scheme 9. Deacylation in step (m) using NaOCH$_3$, MeOH at room temperature for 2 hours produced the second intermediate, after which esterification with succinic anhydride, DMAP, pyridine at 60° C. for 15 hours in step (i) produced compound 14.

Reaction Scheme 9

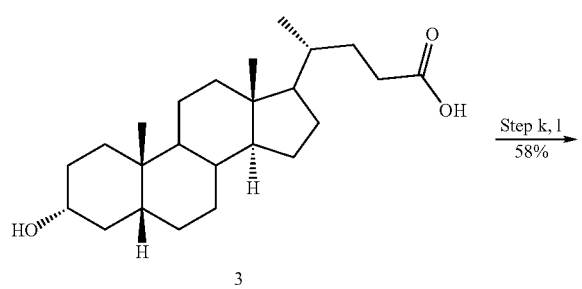

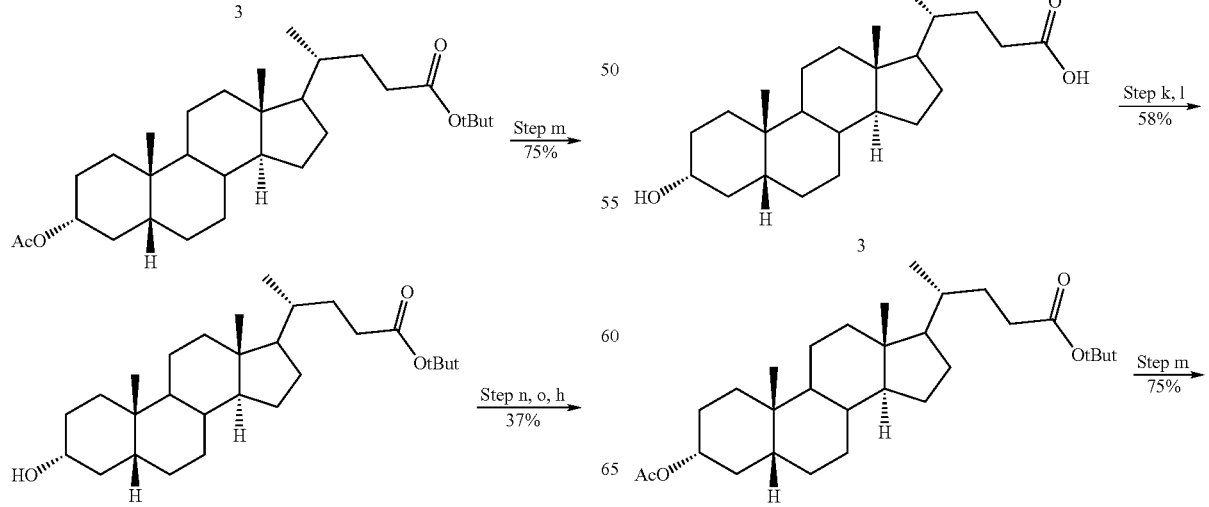

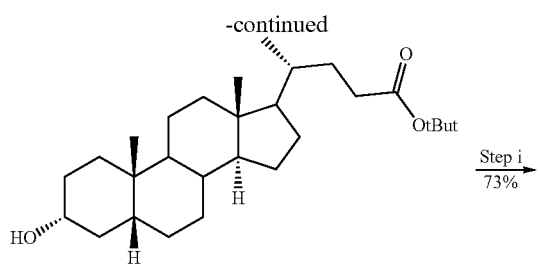

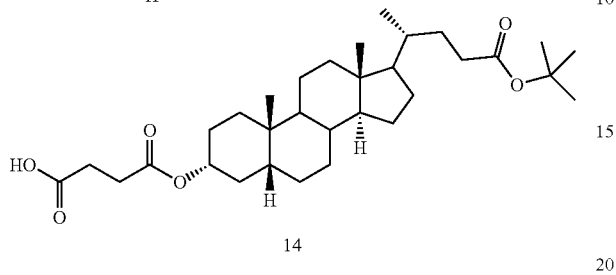

tected amino acid H-Gly-OBut was performed in step (e) using 2-(1H-benzotriazol-1-yl)-1,1,3,3-tetramethyluronium hexafluorophosphate (HBTU)/diisopropylethylamine (DIPEA) as coupling agent in N,N-dimethylformamide (DMF) at room temperature for 30 minutes to give the protected intermediate. Esterification of the intermediate with succinic anhydride, DMAP, pyridine at 80° C. for 15 hours (step g) followed by TFA, 2% H₂O at room temperature for 1 hour (step h) resulted in compound 15.

Synthesis of Compound 15: 4-((3R,5R,10S,13R,14S)-17-((R)-5-(carboxymethylamino)-5-oxopentan-2-yl)-10,13-dimethyl-hexadecahydro-1H-cyclopenta[a]phenanthren-3-yloxy)-4-oxobutanoic acid

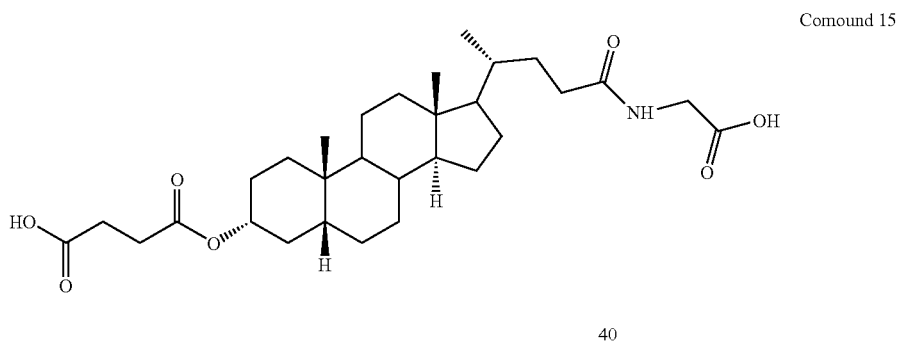

Compound 15 was synthesized from compound 3 according to Reaction Scheme 10. Condensation of 3 and the pro- Reaction Scheme 10

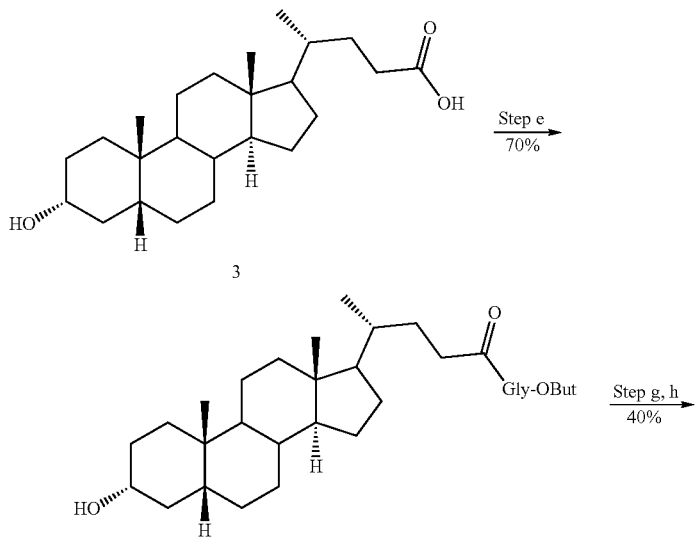

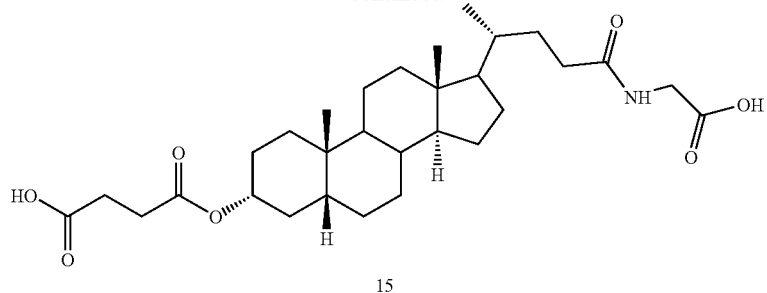

15

Synthesis of Compound 16: (S)-2-((R)-4-((3R,5R,10S,13R,14S)-3-(3-carboxypropanoyloxy)-10,13-dimethyl-hexadecahydro-1H-cyclopenta[a]phenanthren-17-yl)pentanamido)succinic acid luronium hexafluorophosphate (HBTU)/diisopropylethylamine (DIPEA) as coupling agent in N,N-dimethylformamide (DMF) at room temperature for 30 minutes to give the protected intermediate. Esterification of the Compound 16

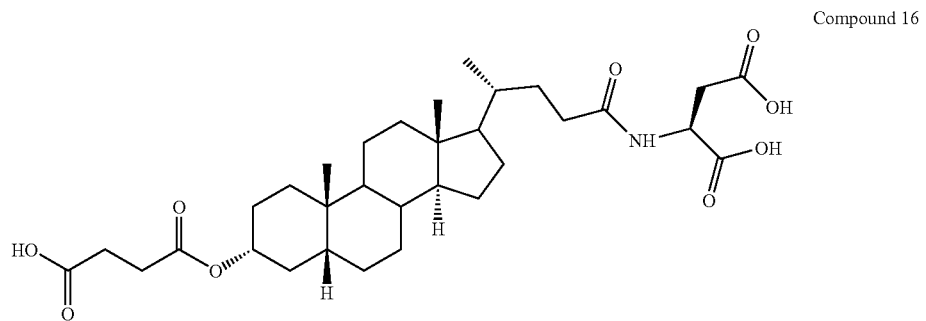 [SMILES: C[C@H](CCC(=O)N[C@@H](CC(=O)O)C(=O)O)C1CC[C@H]2C3CC[C@@H]4C[C@H](OC(=O)CCC(=O)O)CC[C@]4(C)C3CC[C@]12C]

Compound 16 was synthesized from compound 3 according to Reaction Scheme 11. Condensation of 3 and the protected amino acid L-H-Asp(OBut)-OBut was performed in step (e) using 2-(1H-benzotriazol-1-yl)-1,1,3,3-tetramethyintermediate with succinic anhydride, DMAP, pyridine at 80° C. for 15 hours (step g) followed by TFA, 2% H₂O at room temperature for 1 hour (step h) resulted in compound 16.

Reaction Scheme 11

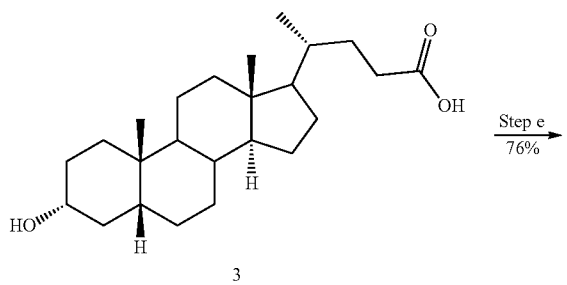

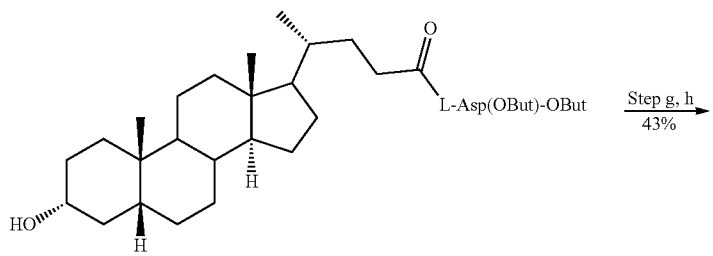

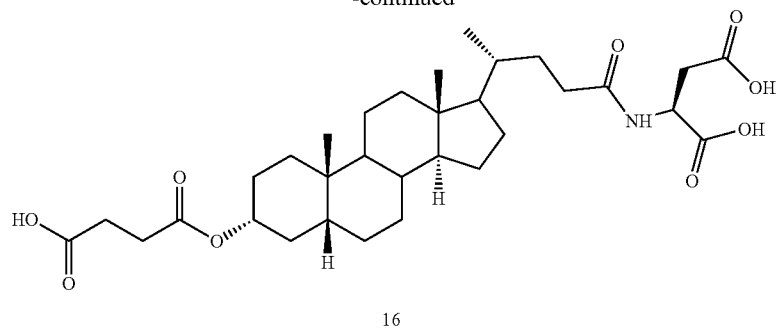

16

Synthesis of Compound 17: (R)-4-((3R,5R,10S,13R, 14S)-3-((R)-2-amino-3-carboxypropanoyloxy)-10, 13-dimethyl-hexadecahydro-1H-cyclopenta[a] phenanthren-17-yl)pentanoic acid Compound 17

Compound 17 was synthesized from compound 3 according to Reaction Scheme 12. To prepare compound 17, the hydroxyl group of 3 was transformed to an acetyl group in step (k) using acetic anhydride, pyridine, at room temperature for 5 hours followed by an esterification step (step l) with t-BuOH, DMAP, DCC, DCM; at room temperature for 30 minutes to give the first intermediate in Reaction Scheme 12. Deacylation in step (m) using NaOCH$_3$, MeOH at room temperature for 2 hours produced the second intermediate, which was converted to the desired product 17 by dicyclohexylcarbodiimide (DCC)-promoted coupling followed by deprotection of the Fmoc, Boc, and tBu groups in three steps: (p) Fmoc-D-Asp(OBut)-OH, DMAP, DCC, DCM at room temperature for 30 minutes; (O) DBU, DCM room temperature for 1 hour; and (h) TFA, 2% H$_2$O at room temperature for 1 hour.

Reaction Scheme 12

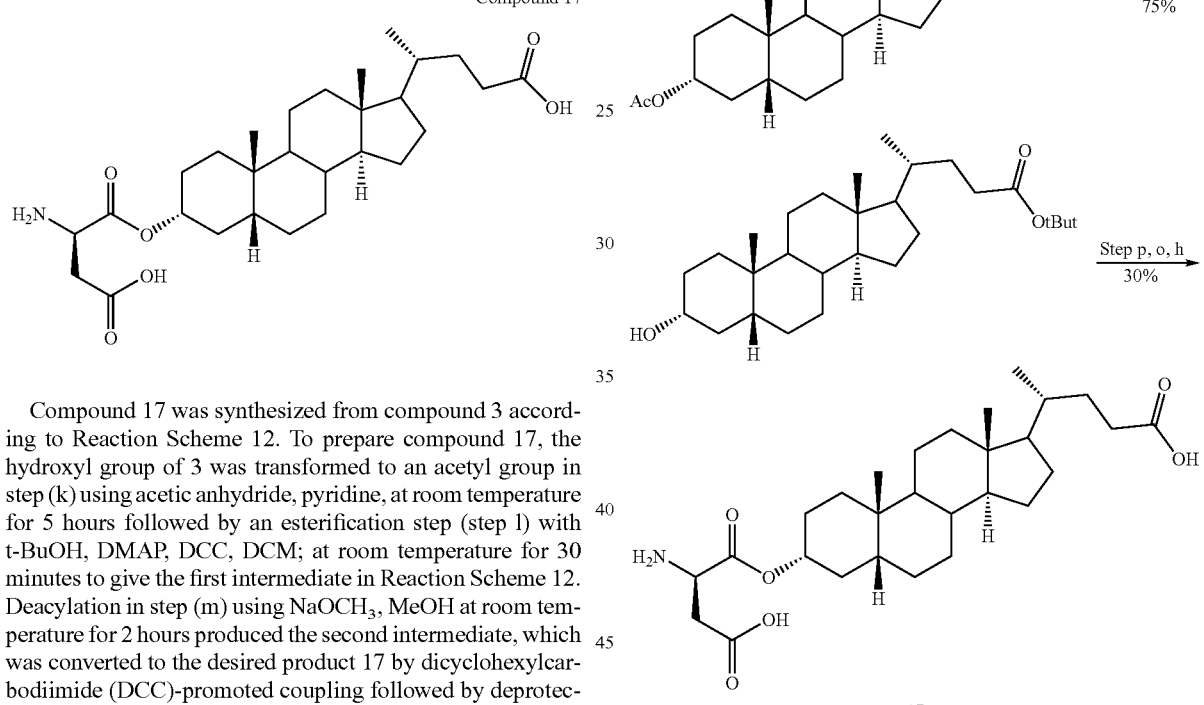

17

Synthesis of Compound 18: (3R,5R,10S,13R,14S)-17-((R)-5-(4-(2-hydroxyethyl)-1H-1,2,3-triazol-1-yl) pentan-2-yl)-10,13-dimethyl-hexadecahydro-1H-cyclopenta[a]phenanthren-3-ol Compound 18

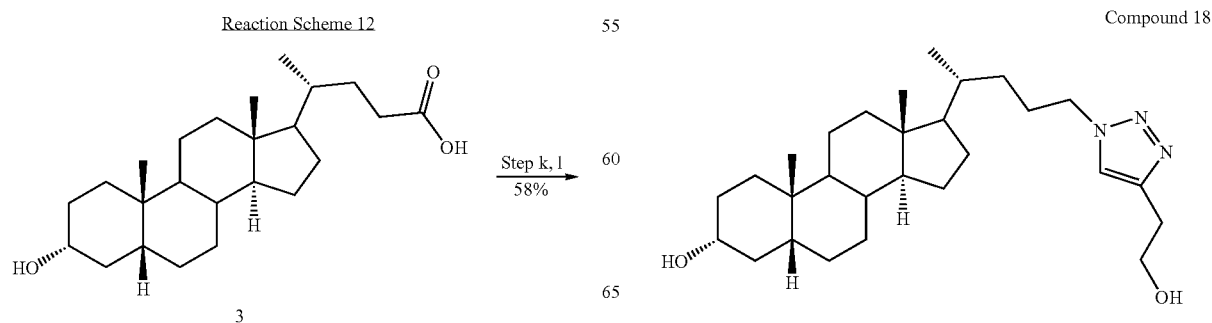

Compound 18 was synthesized from compound 8 according to Reaction Scheme 13. The conversion of compound 8 to the corresponding azide intermediate was achieved in step (d) in the presence of excess sodium azide (NaN$_3$), a catalytic amount of tetrabutylammonium iodide (TBAI), and 15-crown-5 at 110° C. for 15 hours. Preparation of the 1,4-disubstituted 1,2,3-triazole compound 18 was achieved in step (q) using copper(I)-catalyzed ligation of the azide intermediate with the appropriate alkyne using click chemistry.

Compound 19 was synthesized from compound 8 according to Reaction Scheme 14. Conversion of compound 8 to the corresponding azide intermediate was achieved in step (d) in the presence of excess sodium azide (NaN$_3$), a catalytic amount of tetrabutylammonium iodide (TBAI), and 15-crown-5 at 110° C. for 15 hours. Preparation of a 1,4-disubstituted 1,2,3-triazole intermediate was achieved in step (q) using copper(I)-catalyzed ligation of the azide intermediate with the appropriate alkyne. Subsequent Boc deprotection in TFA, 2% H$_2$O at room temperature for 1 hour in step (h) afforded the racemic derivative 19.

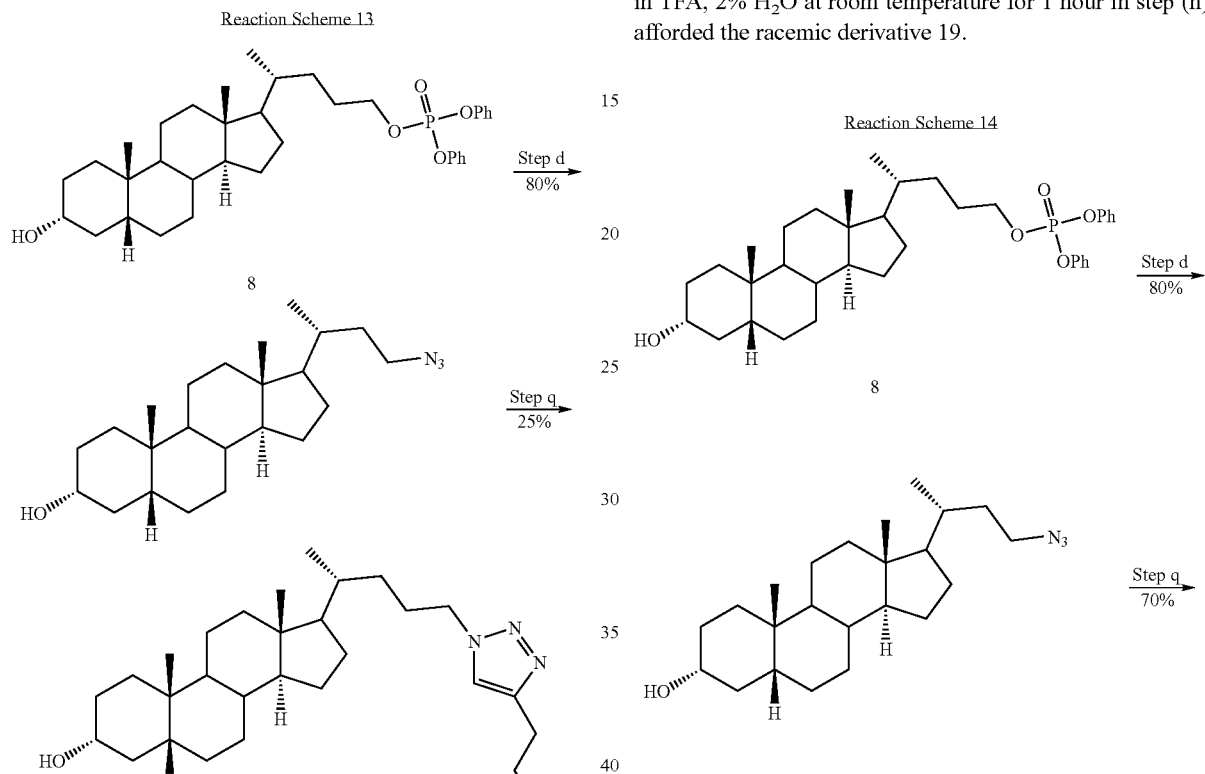

Synthesis of Compound 19: 2-amino-3-(1-((R)-4-((3R,5R,10S,13R,14S)-3-hydroxy-10,13-dimethyl-hexadecahydro-1H-cyclopenta[a]phenanthren-17-yl)pentyl)-1H-1,2,3-triazol-4-yl)propanoic acid

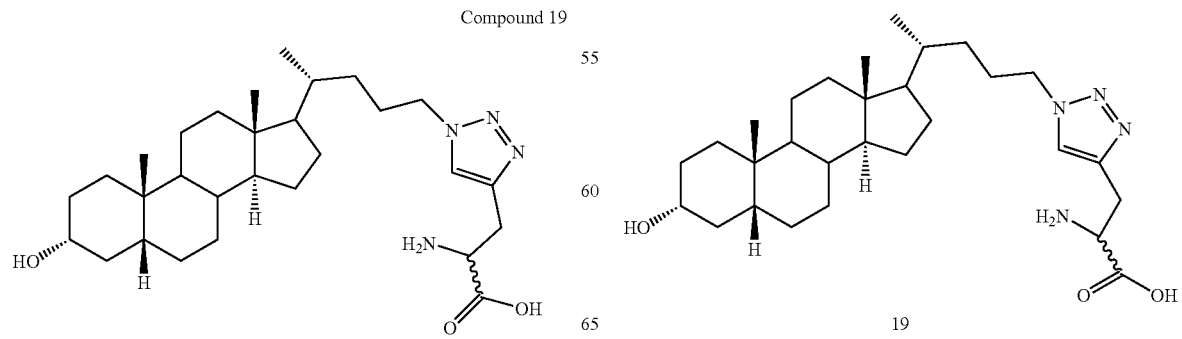

Synthesis of Compound 20: 2-(diethoxyphosphoryl)-3-(1-((R)-4-((3R,5R,10S,13R,14S)-3-hydroxy-10,13-dimethyl-hexadecahydro-1H-cyclopenta[a]phenanthren-17-yl)pentyl)-1H-1,2,3-triazol-4-yl)propanoic acid

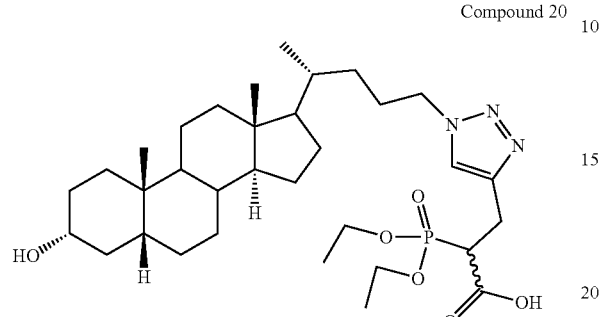

Compound 20

Compound 20 was synthesized from compound 8 according to Reaction Scheme 15. Conversion of compound 8 to the corresponding azide intermediate was achieved in step (d) in the presence of excess sodium azide (NaN$_3$), a catalytic amount of tetrabutylammonium iodide (TBAI), and 15-crown-5 at 110° C. for 15 hours. Preparation of a 1,4-disubstituted 1,2,3-triazole intermediate was achieved in step (q) using copper(I)-catalyzed ligation of the azide intermediate with the appropriate alkyne. Subsequent saponification in NaOH, EtOH/H$_2$O (1:1) at room temperature for 5 hours in step (r) afforded the racemic derivative 20.

Reaction Scheme 15

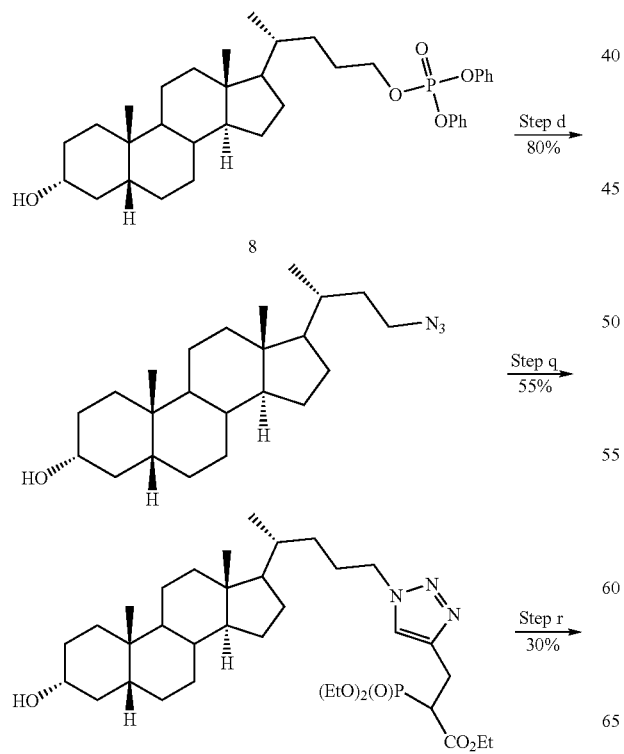

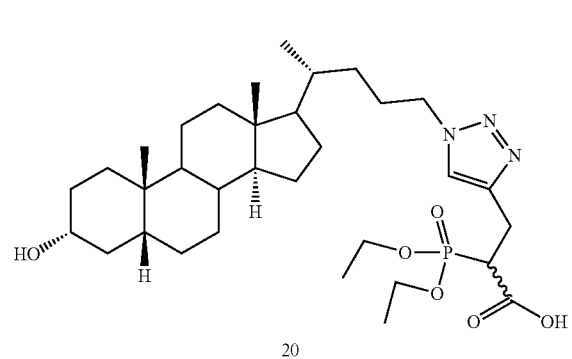

Synthesis of Compound 21: 3-(1-((R)-4-((3R,5R,10S,13R,14S)-3-hydroxy-10,13-dimethyl-hexadecahydro-1H-cyclopenta[a]phenanthren-17-yl)pentyl)-1H-1,2,3-triazol-4-yl)propanoic acid

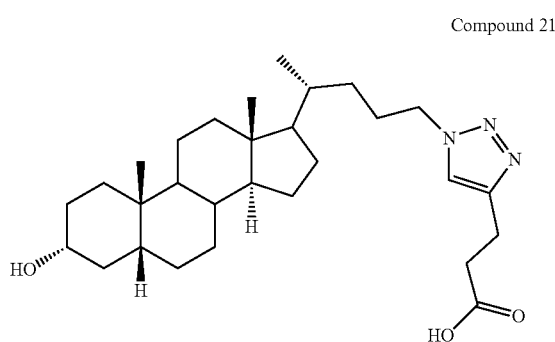 [SMILES: C[C@H](CCCn1cc(CCC(=O)O)nn1)C1CC[C@H]2C3CC[C@@H]4C[C@H](O)CC[C@]4(C)C3CC[C@]12C]

Compound 21

Compound 21 was synthesized from compound 8 according to Reaction Scheme 16. Conversion of compound 8 to the corresponding azide intermediate was achieved in step (d) in the presence of excess sodium azide (NaN$_3$), a catalytic amount of tetrabutylammonium iodide (TBAI), and 15-crown-5 at 110° C. for 15 hours. Preparation of the 1,4-disubstituted 1,2,3-triazole compound 21 was achieved in step (q) using copper(I)-catalyzed ligation of the azide intermediate with the appropriate alkyne.

Reaction Scheme 16

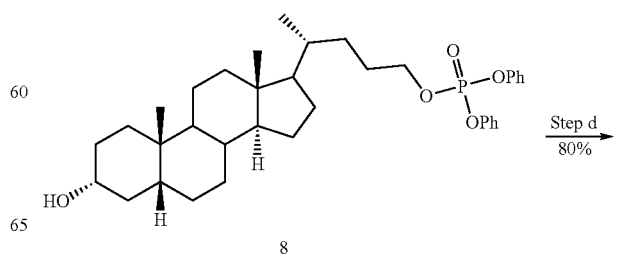

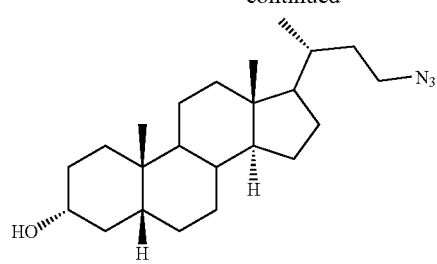

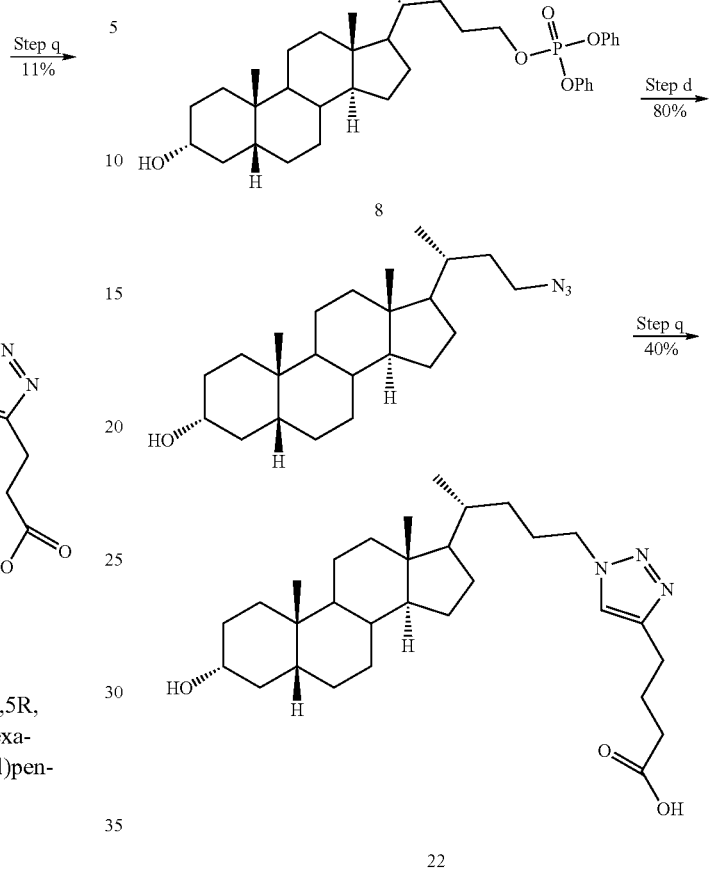

Reaction Scheme 17

Synthesis of Compound 22: 4-(1-((R)-4-((3R,5R, 10S,13R,14S)-3-hydroxy-10,13-dimethyl-hexa-decahydro-1H-cyclopenta[a]phenanthren-17-yl)pentyl)-1H-1,2,3-triazol-4-yl)butanoic acid

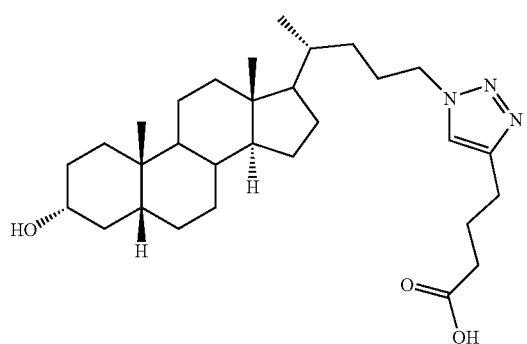

Compound 22

Compound 22 was synthesized from compound 8 according to Reaction Scheme 17. Conversion of compound 8 to the corresponding azide intermediate was achieved in step (d) in the presence of excess sodium azide (NaN₃), a catalytic amount of tetrabutylammonium iodide (TBAI), and 15-crown-5 at 110° C. for 15 hours. Preparation of the 1,4-disubstituted 1,2,3-triazole compound 22 was achieved in step (q) using copper(I)-catalyzed ligation of the azide intermediate with the appropriate alkyne.

Each compound was tested for α-2,3-ST inhibition using CMP-Neu5Ac as a substrate and a modified disaccharide with a 4,5-dimethoxy-2-nitrobenzyl group as a UV-labeled acceptor. Specifically, inhibition assays were performed in triplicate in reaction solution containing 200 mM MES buffer, 100 mM sodium chloride, 0.5 mM disodium-EDTA, 0.01% Triton X-100, 20 µM modified disaccharide, 1.4 mU α-2,3-ST and inhibitor (in dimethyl sulfoxide) in a total volume of 55. Reactions were incubated at 37° C. for 10 minutes at which point 1 mM CMP-Neu5Ac (to a final concentration 3 µM) was added. The solution was then incubated at 37° C. until a detectable amount of product was produced. The reaction was terminated by quenching the solution mixture with heat at 100° C. for 5 minutes. Enzyme activity was determined by monitoring the quantity of sialylated disaccharide product produced over time at 348 nm by RP-HPLC (Supelco Discovery® HS C18, 5 µm, 4.6 mm×25 cm). Retention time of the product was 20.38 minutes.

The described sixteen synthetic analogues showed decreased $IC_{50}$ s compared to lithocholic acid (Table 1). The terminal alcohol 7 and its derivative 8 displayed a 5 to 17-fold decrease over lithocholic acid, suggesting that a carboxylic acid group is important for promoting, affinity. This was further confirmed by using peptide coupling to extend the terminal carboxylic acid; the inhibitor), properties of compounds 9 and 10 can be restored completely compared to those of 7-8. To determine the importance of the 3-hydroxyl position of lithocholic acid, the inhibition of α-2,3-ST activity by compound 11, which has a ketone moiety in place of a hydroxyl group, was evaluated. Compound 11 was found to have an IC$_{50}$ of 139 μM, representing a 7-fold lower potency than lithocholic acid. Furthermore, compounds 12 and 13 exhibited a 2-fold potency over lithocholic acid, indicating that construction of the 3-hydroxyl portion of lithocholic acid is tunable to the interaction of binding affinity. When the terminal carboxylic acid of 12 was varied, the analogues 14-16 appeared to reach a low micromolar affinity plateau (Table 1). Surprisingly, replacement of the L-Asp with D-Asp, as in 17, gave a 2-fold improvement in potency over 13. In addition, lithocholic acid was further optimized by replacing the carboxylic acid with a 1,4-disubstituted 1,2,3-triazole ligand. Compounds 20 and 21 showed an 8-12-fold potency increase over 19, suggesting that adding a positively charged amino group could abolish affinity. The primary alcohol 18 was at least 10-fold less potent than 21 and 20-fold less potent than 22, consistent with previous observations concerning the value of the terminal carboxylic acid in binding. Analogue 22 was the most active compound with an IC$_{50}$ of 5 μM.

TABLE 1

| Compound | # | IC$_{50}$ (μM) |
|---|---|---|
| | 7 | 351 |
| | 8 | >100 |
| | 9 | 25 |
| | 10 | 16 |

TABLE 1-continued

| Compound | # | IC$_{50}$ (μM) |
|---|---|---|
| | 11 | 139 |
| | 12 | 12 |
| | 13 | 12 |
| | 14 | 13 |
| | 15 | 22 |

TABLE 1-continued

| Compound | # | IC$_{50}$ (μM) |
|---|---|---|
| | 16 | 18 |
| | 17 | 6 |
| | 18 | >100 |
| | 19 | 83 |
| | 20 | 7 |

TABLE 1-continued

| Compound | # | IC$_{50}$ (μM) |
|---|---|---|
| 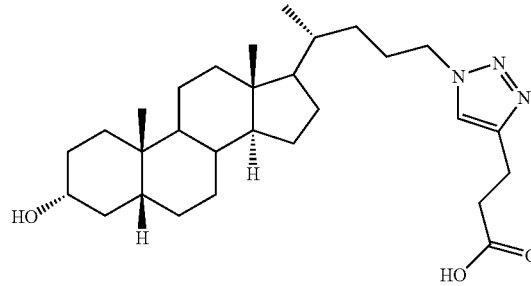 | 21 | 10 |
| 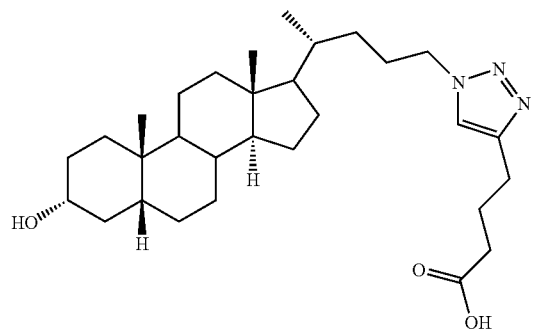 [SMILES: C[C@H](CCCn1cc(CCCC(=O)O)nn1)C1CC[C@H]2C3CC[C@@H]4C[C@H](O)CC[C@]4(C)C3CC[C@]12C] | 22 | 5 |

The inhibition constant ($K_i$) of the most active compound, compound 22, was determined. Reactions were prepared in inhibition assay reaction solution described above and were incubated for 10 minutes after which 0.3, 0.15, and 0.037 mM CMP-Neu5Ac was added in the presence of inhibitor at 5, 4.5, 3.5, 2.5, and 0 μM. Assays were performed in duplicate for each substrate and inhibitor concentration. Velocity was obtained as described under IC$_{50}$ assay conditions, and for each inhibitor concentration, linear relations were generated between the inverse of the velocity and the inverse substrate concentration. The absolute $K_i$ value was determined from the horizontal intercept of a Lineweaver-Burk plot with velocity on the vertical axis and inhibitor concentration on the horizontal axis (FIG. 1). Compound 22 exhibits a noncompetitive inhibition toward CMP-Neu5Ac with a $K_i$ equal to 2.2 μM.

Example 2

Figure 2:
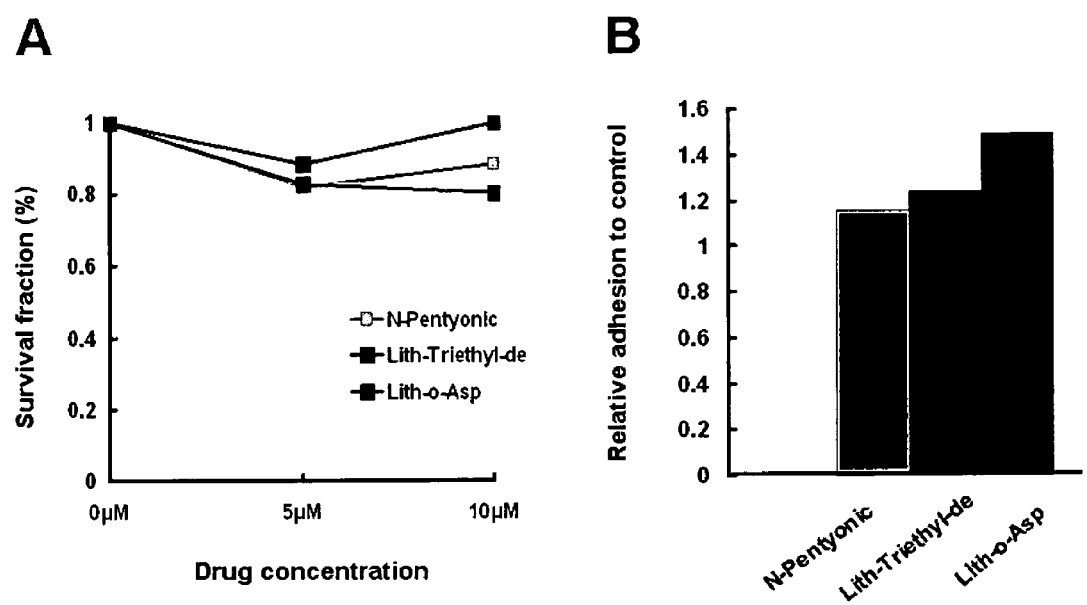
FIG. 2 (A) Cytotoxicity of three α-2,3-ST inhibitors—N-Pentyonic (compound 21), Lith-Triethyl-de (compound 20), and Lith-o-Asp (compound 13)—on CL1-5 lung cancer cells after 48 hours treatment with 5 μM and 10 μM inhibitor. Survival fraction is calculated as a percentage of DMSO treated control cells. (B) Adhesion of CL1-5 cells treated with α-2,3-ST inhibitors to type-I collagen relative to the basal level of adhesion (equal to 1) by DMSO treated control cells.

Lithocholic Acid Analog α-2,3-ST Inhibitors Suppress Growth and Enhance Adhesion of CL1-5 Lung Cancer Cells To determine the effect of the synthesized membrane-permeable α-2,3-ST inhibitors disclosed in Example 1 on cellular processes, in vitro cytotoxicity and adhesion assays were performed on the highly metastatic lung cancer cell line CL1-5. CL1-5 cells were plated at 1×10$^6$ cells per 60 mm culture dish in DMEM containing 10% fetal bovine serum (FBS) in 5% CO$_2$. The following day the media was replaced with FBS-free media containing inhibitors at 5 μM or 10 μM concentration in DMSO. Controls cells were treated with 0.1% DMSO-containing medium without inhibitor. Cell number and viability were determined 48 hours later by trypan blue exclusion. Treatment with three α-2,3-ST inhibitors, N-Pentyonic (compound 21), Lith-Triethyl-de (compound 20), and Lith-o-Asp (compound 13), inhibited CL1-5 cell growth by between 10-20% compared to control (FIG. 2A).

In addition to an effect on cell viability, treatment with α-2,3-ST inhibitors significantly increased adhesion of CL1-5 cells to the extracellular matrix protein collagen 1. Ninety-six-well microplates were pre-coated with collagen type I (100 μg/ml, 40 μl/well) then blocked by 5% bovine serum albumin (BSA) at 4° C. CL1-5 cells (5×10$^4$ per experimental condition) were treated with varying doses of an α-2,3-ST inhibitor or DMSO control, seeded onto pre-coated wells, and incubated for 4 hours at 37° C. in 5% CO$_2$. Cells were washed twice with serum-free DMEM medium to remove unattached cells, and then fixed with 1% formaldehyde for 10 minutes at 4° C. Fixed cells were stained with crystal violet for 25 minutes and then lysed with 1% SDS solution. The number of attached cells was determined by correlation to absorbance at 590 nm. Treatment with α-2,3-ST inhibitors resulted in a 1.2-1.5 fold increase in adhesion of CL1-5 cells to collagen I (FIG. 2B).

Example 3

Inhibition of α-2,3-ST Decreases CL1-5 Lung Cancer Cell Migration

Figure 3:
FIG. 3 shows the result of a wound healing assay 48 hours after treatment of CL1-5 cells with DMSO control (A) and 10 μM Lith-o-Asp (B). The α-2,3-ST inhibitor Lith-O-Asp inhibited cell migration of cells into a "wound" created by scraping cells from the culture dish.
Figure 3:

To assess the effect of α-2,3-ST inhibition on cell migration, a wound healing assay was used. Highly metastatic CL1-5 lung cancer cells were pretreated with 10 μM α-2,3-ST inhibitor Lith-o-Asp for 48 hours in DMEM containing 10% FBS at 5% CO$_2$. A section of cells was then scraped from the culture plate to form a gap, and cell migration into the "wound" was observation over 48 hours in the continuous presence of α-2,3-ST inhibitor. Compared to DMSO control treated cells, Lith-o-Asp significantly decreased the migration ability of CL1-5 cells (FIG. 3).

Example 4

Figure 4:
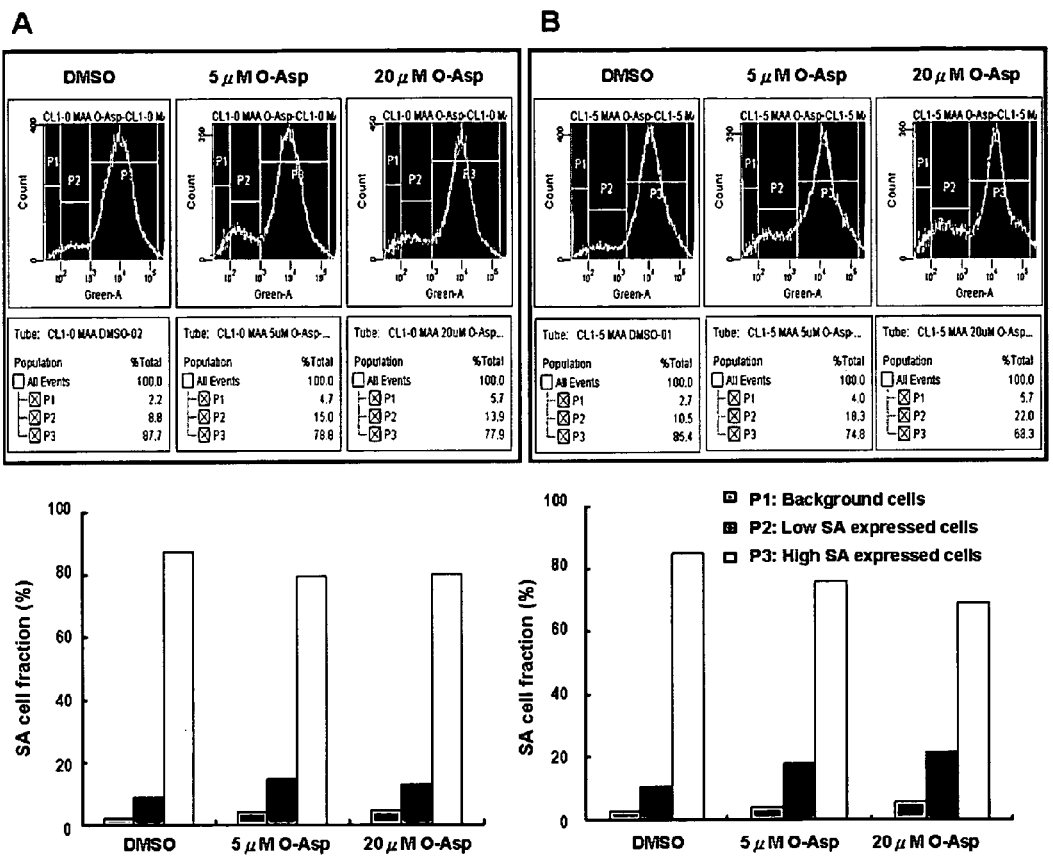
FIG. 4 shows the expression level of cell surface α-2,3-sialylated antigens (SA) on low metastatic CL1-1 cells (A) and highly metastatic CL1-5 cells (B). Upper panels show results from FLOW cytometry: P1 is cells at background intensity; P2 and P3 are cells expressing SA at low and high intensities, respectively; and percentages are calculated for each from all detected events. Lower graphs show the average fluorescence intensity values of experiments plotted into a column chart.

Inhibition of α-2,3-ST Decreases Cell Surface Expression of α-2,3 Sialylated Antigens on Lung Cancer Cells To determine whether α-2,3-ST inhibition alters cell surface glycosylation, lung cancer cells were treated with Lith-o-Asp and cell surface α-2,3-sialylated antigens were detected by FLOW cytometry. Cells were treated with α-2,3-ST inhibitor for five days after which $1\times10^6$ lung cancer cells were collected and washed twice with Hank's balanced salt solution (HBSS). Collected cells were incubated with FITC-conjugated MAL (1:50) at 37° C. for 15-20 minutes, non-binding MAL was removed by washing with HBSS, and $3\times10^4$ cells were detected on a FACScalibur instrument (Becton Dickinson). Two different lung cancer cell lines were tested: CL1-1 with low metastatic potential and CL1-5 with high metastatic potential. Since CL1-5 cells were derived from the CL1-1 line by an in vitro matrix gel invasion assay (Chen et al., Cancer Res., 2001, 61:5223), these cell lines share the same genetic background. Treatment of CL1-1 cells with Lith-o-Asp reduced expression of α-2,3-sialylated antigens to around 15% of DMSO treated control cells at both 5 μM and 20 μM (FIG. 4A). In contrast, Lith-o-Asp inhibited the expression of cell surface α-2,3-sialylated antigens in the highly metastatic CL1-5 lung cancer cells in a dose-dependent manner of greater than 15% (FIG. 4B).

Example 5

Figure 5:
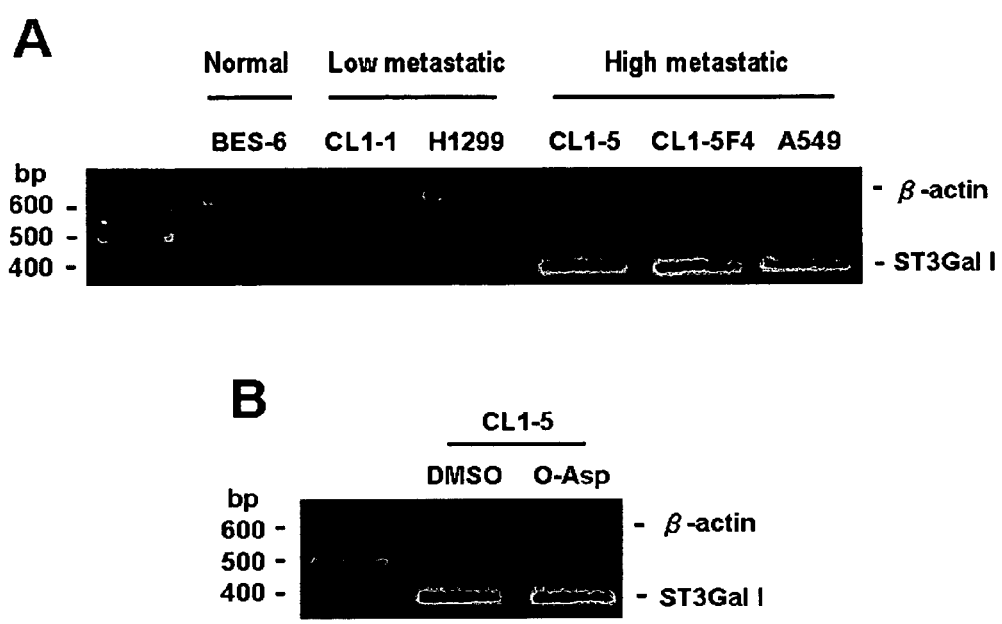
FIG. 5 shows endogenous mRNA expression levels of ST3Gal I compared to β-actin in lung cells showing various metastasis potentials as indicated (A). (B) The mRNA expression of ST3Gal I gene is unchanged in CL1-5 cells treated with either DMSO or Lith-o-Asp.

Expression of ST3Gal I in Various Cell Lines and Following Inhibition of α-2,3-ST To evaluate the effect of α-2,3-ST inhibition on endogenous gene expression, mRNA expression of ST3Gal I was measured by semi-quantitative reverse transcriptase (RT)-PCR in various cell lines with different metastasis potentials. Cell lines analyzed included: normal lung epithelial BES-6 cells; low metastasis CL1-1 and H1299 lung cancer cells; and high metastasis CL1-5, CL1-5 F4, and A549 lung cancer cells. Cells were incubated with α-2,3-ST inhibitor for 48 hours and then collected for RNA extraction by TRIzol (Invitrogen) and phenol/chloroform. After a RT reaction, complementary DNA was amplified by PCR using ST3Gal I-specific primers: forward 5'-GGACCCTGAAAGTGCTCA-3' (SEQ ID NO.: 1) and reverse 5'-TCTCCAGCATAGGGTCCA-3' (SEQ ID NO.: 2). PCR conditions were as follows: denaturation at 95° C., annealing at 61° C., and polymerization at 72° C. for 35 cycles. The relative levels of mRNA expression were determined by comparison to the value of an internal standard (β-actin) in each reaction. PCR products for the ST3Gal I gene and the β-actin sequence were mixed and resolved by electrophoresis at 120 V for 30 minutes on a 1.5% ethidium bromide stained gel in 0.5×TBE. Expression of ST3Gal I was undetectable in the normal cells, but expression was markedly increased in cells with high metastasis potential compared to those with low metastasis potential (FIG. 5A). Furthermore, treatment with α-2,3-ST inhibitor Lith-o-Asp did not significantly reduce mRNA expression of the ST3Gal I gene in CL1-5 lung cancer cells (FIG. 5B).

Example 6

Inhibition of α-2,3-ST Alters Protein Expression in CL1-5 Lung Cancer Cells

To determine whether α-2,3-ST inhibition affects protein expression in CL1-5 lung cancer cells, two-dimensional electrophoresis (2DE) using a staining system specific for phosphoproteins was performed. CL1-5 cells were treated with 10 μM Lith-o-Asp or DMSO alone for 48 hours after which cells were collected ($1\times10^7$ cells for each experimental condition), and the cell pellets solubilized in lysis buffer containing 8% Urea (Boehringer Mannheim, Germany), 2M thiourea (Aldrich, Wis., USA), and 4% CHAPS (J. T. Baker, N.J., USA). After sonication, 1 mg of total protein was loaded into immobilized pH gradient (IPG) gel strips (pH 3-10, 18 cm long, Amersham Pharmacia Biotech, Uppsala, Sweden), which had been rehydrated overnight prior to use in a solution of 7 M urea, 2 M thiourea, 4% CHAPS, 40 mM Tris-base, 2% IPG ampholyte, 65 mM DTE, and 0.0002% bromophenol blue. For the first dimensional separation, isoelectric focusing was carried out using the IPGphor system (Amersham Pharmacia Biotech) at 20° C. with 7000 V for a total of 65 kVh. After isoelectric focusing, the IPG strips were equilibrated for 15 minutes in equilibration solution (50 mM Tris-HCl, pH 8.8, 6 M urea, 2% SDS, 30% glycerol, 2% DTE), then attached with 0.5% agarose to the top of a vertical 12.5% linear gradient SDS-polyacrylamide gel. Second dimensional electrophoresis was carried out at 45 mA per gel for 5 hours until the bromophenol blue reached the bottom of the gel. The 2-D electrophoresis gels were stained with Pro-Q Diamond PhosphoProtein Gel Stain (Molecular Probes, Oreg., USA) for 3 hours, fixed in a solution of 10% methanol and 7% acetic acid for 30 minutes, and then soaked in deionized water for 20 minutes to remove residual dye. The gels were digitally scanned using fluorescence image scanning Gel Logic 200 Imaging System (Kodak, N.Y., USA), and protein spots were automatically detected and analyzed using ImageMaster software (Amersham Bioscience).

Figure 6:
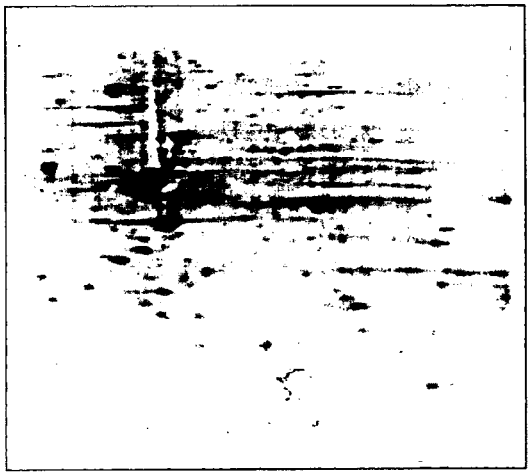
FIG. 6 shows 2DE electrophotograms of (A) DMSO control and (B) Lith-o-Asp treated CL1-5 lung cancer cells. The IEF was pH 3-10, and the molecular weight was 21.0-97.0 kDa. Differentially expressed proteins were further identified by MS and MS/MS.
Figure 6:
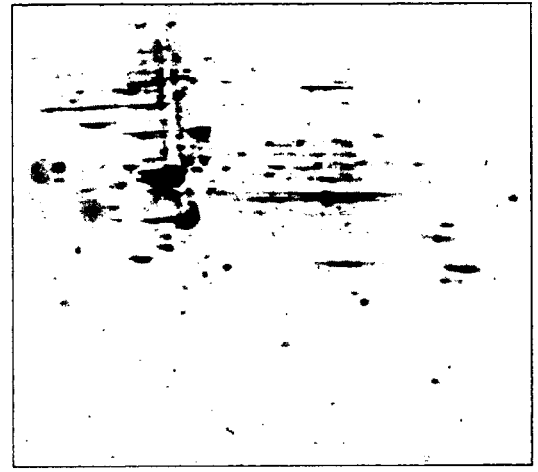

Lith-o-Asp treatment of CL1-5 lung cancer cells revealed four spots with increased intensity and forty-nine spots with decreased intensity on processed 2-D gels (FIG. 6). These protein spots were digested in-gel using trypsin and were analyzed by a tandem mass spectrum (MS/MS) to determine their identity. Several proteins involved in signaling and damage response pathways were identified including heat shock protein 75, phosphoglycerate kinase 1, Ran-GTPase activating protein 1, and WD-repeat containing protein 1.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. At least one chemical entity chosen from the compounds of Formula I:

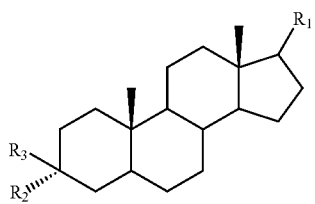

(Formula I)

and pharmaceutically acceptable salts thereof, wherein
   $R_1$ is —$CHR_4(CH_2)_nR_5$ where
   n is chosen from 2 and 3,
   $R_4$ is chosen from hydrogen and optionally substituted lower alkyl; and
   $R_5$ is an optionally substituted triazole;
   $R_2$ is chosen from hydroxy and acyloxy;
   $R_3$ is hydrogen, or $R_2$ and $R_3$, taken together with the carbon to which they are attached, form an oxo group.

2. The at least one chemical entity of claim 1, wherein n is 2.

3. The at least one chemical entity of claim 1, wherein n is 3.

4. The at least one chemical entity of claim 1, wherein $R_4$ is chosen from hydrogen and lower alkyl.

5. The at least one chemical entity of claim 4, wherein $R_4$ is lower alkyl.

6. The at least one chemical entity of claim 5, wherein $R_4$ is methyl.

7. The at least one chemical entity of claim 6, wherein the triazole is substituted with a carboxyl group.

8. The at least one chemical entity of claim 1, wherein $R_5$ is a substituted triazole and wherein the substituent is chosen from lower alkyl substituted with one or two groups chosen from carboxyl, amino, and dialkylphosphonate, and provided that the lower alkyl group is substituted with at least one carboxyl group.

9. The at least one chemical entity of claim 1, wherein $R_3$ is hydrogen.

10. The at least one chemical entity of claim 1, wherein $R_2$ and $R_3$ taken together with the carbon to which they are attached form an oxo group.

11. The at least one chemical entity of claim 1, wherein $R_2$ is —O—C(O)R, and wherein R is alkyl substituted with —$NH_2$ and COOH.

12. The at least one chemical entity of claim 11, wherein R2 is

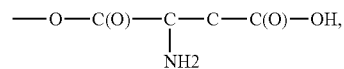

and R3 is hydrogen.

13. At least one chemical entity chosen from
   (3R,5R,10S,13R,14S)-17-((R)-5-(4-(2-hydroxyethyl)-1H-1,2,3-triazol-1-yl)pentan-2-yl)-10,13-dimethyl-hexadecahydro-1H-cyclopenta[a]phenanthren-3-ol;
   2-amino-3-(1-((R)-4-((3R,5R,10S,13R,14S)-3-hydroxy-10,13-dimethyl-hexadecahydro-1H-cyclopenta[a]phenanthren-17-yl)pentyl)-1H-1,2,3-triazol-4-yl)propanoic acid;
   2-(diethoxyphosphoryl)-3-(1-((R)-4-((3R,5R,10S,13R,14S)-3-hydroxy-10,13-dimethyl-hexadecahydro-1H-cyclopenta[a]phenanthren-17-yl)pentyl)-1H-1,2,3-triazol-4-yl)propanoic acid;
   3-(1-((R)-4-((3R,5R,10S,13R,14S)-3-hydroxy-10,13-dimethyl-hexadecahydro-1H-cyclopenta[a]phenanthren-17-yl)pentyl)-1H-1,2,3-triazol-4-yl)propanoic acid;
   4-(1-((R)-4-((3R,5R,10S,13R,14S)-3-hydroxy-10,13-dimethyl-hexadecahydro-1H-cyclopenta[a]phenanthren-17-yl)pentyl)-1H-1,2,3-triazol-4-yl)butanoic acid; and pharmaceutically acceptable salts thereof.

14. A pharmaceutical composition comprising a therapeutically effective amount of the at least one chemical entity of claim 1 and a pharmaceutically acceptable vehicle.

15. A method for inhibiting α-2,3-sialyltransferase activity, comprising contacting lung cancer cells expressing α-2,3-sialyltransferase with the at least one chemical entity of claim 1 in an amount sufficient to detectably decrease the level of sialylation of glycoconjugates in the lung cancer cells.

16. The method of claim 15, wherein the lung cancer cells are undergoing cell migration.

17. The method of claim 16, wherein the cell migration is associated with cancer metastasis.

18. The method of claim 15, wherein the lung cells are present in a mammal.

19. The method of claim 18, wherein the mammal is a human.

20. A method for slowing the development of lung cancer, or relieving lung cancer in a patient, comprising administering to the patient a therapeutically effective amount of the at least one chemical entity of claim 1.

21. The method of claim 20, wherein the cancer is undergoing metastasis.

22. The method of claim 20, wherein the patient is a human.

23. The method of claim 20, further comprising administering at least one additional therapeutic agent appropriate for effecting combination therapy.

24. A method for inhibiting α-2,3-sialyltransferase activity in vitro, comprising contacting cells expressing α-2,3-sialyltransferase with the at least one chemical entity of claim 1 in an amount sufficient to detectably decrease the level of sialylation of glycoconjugates.

* * * * *

SEQUENCE LISTING

<160> NUMBER OF SEQ ID NOS: 2

<210> SEQ ID NO 1
<211> LENGTH: 18
<212> TYPE: DNA

```
<213> ORGANISM: Artificial Sequence
<220> FEATURE:
<223> OTHER INFORMATION: Primer

<400> SEQUENCE: 1
ggaccctgaa agtgctca                                               18

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
tctccagcat agggtcca                                               18
```